US012629167B2

(12) United States Patent (10) Patent No.: US 12,629,167 B2
Deeny et al. (45) Date of Patent: *May 19, 2026

(54) SURGICAL TOOL ARRANGEMENT AND SURGICAL CUTTING ACCESSORY FOR USE THEREWITH

(71) Applicant: Stryker Corporation, Kalamazoo, MI (US)

(72) Inventors: Bryan G. Deeny, Ballincollig (IE); James M. Hayes, Sunnyvale, CA (US); Brian Fouts, Morgan Hill, CA (US)

(73) Assignee: Stryker Corporation, Kalamazoo, MI (US)

( * ) Notice: Subject to any disclaimer, the term of this patent is extended or adjusted under 35 U.S.C. 154(b) by 340 days.

This patent is subject to a terminal disclaimer.

(21) Appl. No.: 18/109,594

(22) Filed: Feb. 14, 2023

(65) Prior Publication Data

US 2023/0190326 A1 Jun. 22, 2023

Related U.S. Application Data

(63) Continuation of application No. 16/593,224, filed on Oct. 4, 2019, now Pat. No. 11,612,407, which is a
(Continued)

(51) Int. Cl.
*A61B 17/32* (2006.01)
*A61B 17/00* (2006.01)
*A61B 90/00* (2016.01)

(52) U.S. Cl.
CPC .................. *A61B 17/32002* (2013.01); *A61B 2017/0046* (2013.01); *A61B 2090/08021* (2016.02); *A61B 2217/005* (2013.01)

(58) Field of Classification Search
CPC .............. A61B 17/32002; A61B 17/32; A61B 2217/005; A61B 2017/32007; A61B 2090/0801; A61B 2090/0821
See application file for complete search history.

(56) References Cited

U.S. PATENT DOCUMENTS 3,732,858 A 5/1973 Banko
3,844,272 A 10/1974 Banko
(Continued)

FOREIGN PATENT DOCUMENTS

AU 3781400 A 7/2000
CA 2398850 A1 8/2001
(Continued)

OTHER PUBLICATIONS

"The Formula For Success" brochure dated 2007 (6 pages).

*Primary Examiner* — Katherine M Rodjom
(74) *Attorney, Agent, or Firm* — Foley & Lardner LLP

(57) ABSTRACT

A surgical tool arrangement for performing endoscopic surgical procedures which includes a powered handpiece and a surgical cutting accessory which detachably connects to the handpiece. The cutting accessory incorporates a cutting head for resecting tissue and a suction arrangement at the distal end of the cutting accessory closely adjacent the cutting head which suction arrangement serves to evacuate tissue from the surgical site and additionally serves as a cleaning mechanism for the surgical cutting accessory. The accessory additionally incorporates a bearing arrangement for supporting the cutting element as same rotates within the housing element.

19 Claims, 12 Drawing Sheets

Related U.S. Application Data continuation of application No. 14/853,434, filed on Sep. 14, 2015, now Pat. No. 10,470,786.

(60) Provisional application No. 62/064,719, filed on Oct. 16, 2014.

(56) References Cited

U.S. PATENT DOCUMENTS

| | | | |
|---|---|---|---|
| 4,445,509 A | 5/1984 | Auth | |
| 4,646,738 A | 3/1987 | Trott | |
| 4,842,578 A | 6/1989 | Johnson et al. | |
| 4,867,157 A | 9/1989 | McGurk-Burleson et al. | |
| 4,983,179 A | 1/1991 | Sjostrom | |
| 5,084,052 A | 1/1992 | Jacobs | |
| 5,217,479 A | 6/1993 | Shuler | |
| 5,269,798 A | 12/1993 | Winkler | |
| 5,366,468 A | 11/1994 | Fucci et al. | |
| 5,489,291 A | 2/1996 | Wiley | |
| 5,492,527 A | 2/1996 | Glowa et al. | |
| 5,592,727 A | 1/1997 | Glowa et al. | |
| 5,601,583 A | 2/1997 | Donahue et al. | |
| 5,620,447 A | 4/1997 | Smith et al. | |
| 5,693,063 A | 12/1997 | Van Wyk et al. | |
| 5,759,185 A | 6/1998 | Grinberg | |
| 5,766,199 A | 6/1998 | Heisler et al. | |
| 5,833,692 A | 11/1998 | Cesarini et al. | |
| 5,833,702 A | 11/1998 | Van Wyk et al. | |
| 5,843,106 A | 12/1998 | Heisler | |
| 5,851,208 A | 12/1998 | Trott | |
| 5,913,867 A * | 6/1999 | Dion | A61B 17/32002 606/180 |
| 6,001,116 A | 12/1999 | Heisler et al. | |
| 6,053,923 A * | 4/2000 | Veca | A61B 17/32002 606/80 |
| 6,053,928 A | 4/2000 | Van Wyk et al. | |
| 6,068,641 A | 5/2000 | Varsseveld | |
| 6,217,598 B1 | 4/2001 | Berman et al. | |
| 6,312,438 B1 | 11/2001 | Adams | |
| 6,312,441 B1 | 11/2001 | Deng | |
| 6,387,110 B1 * | 5/2002 | Drucker | A61B 17/32002 606/180 |
| 6,620,180 B1 | 9/2003 | Bays et al. | |
| 6,827,725 B2 | 12/2004 | Batchelor et al. | |
| 7,077,845 B2 | 7/2006 | Hacker et al. | |
| 7,237,990 B2 | 7/2007 | Deng | |
| 7,618,428 B2 | 11/2009 | O'Quinn et al. | |
| 7,682,333 B2 | 3/2010 | Deng | |
| 7,803,170 B2 | 9/2010 | Mitusina | |
| 7,887,559 B2 | 2/2011 | Deng et al. | |
| 8,062,319 B2 | 11/2011 | O'Quinn et al. | |
| 10,470,786 B2 | 11/2019 | Deeny et al. | |
| 2003/0135151 A1 | 7/2003 | Deng | |
| 2004/0092991 A1 | 5/2004 | Deng | |
| 2004/0220602 A1 | 11/2004 | Deng et al. | |
| 2005/0065538 A1 | 3/2005 | Van Wyk | |
| 2006/0142775 A1 | 6/2006 | Heneberry et al. | |
| 2006/0196038 A1 | 9/2006 | Van Wyk | |
| 2006/0212060 A1 | 9/2006 | Hacker et al. | |
| 2008/0208194 A1 | 8/2008 | Bickenbach | |
| 2010/0298855 A1 | 11/2010 | Dierck | |
| 2011/0238099 A1 | 9/2011 | Loreth | |
| 2012/0150209 A1 | 6/2012 | Gubellini et al. | |
| 2012/0203230 A1 | 8/2012 | Adams | |
| 2013/0274779 A1 | 10/2013 | Kulas et al. | |
| 2013/0304070 A1 | 11/2013 | Nelson et al. | |

FOREIGN PATENT DOCUMENTS

| | | | |
|---|---|---|---|
| CA | 2361354 A1 | 5/2002 | |
| DE | 69732580 T2 | 5/2006 | |
| EP | 0796064 A1 | 9/1997 | |
| EP | 0800793 A1 | 10/1997 | |
| EP | 0836833 A2 | 4/1998 | |
| EP | 1006898 B1 | 6/2000 | |
| EP | 1253863 B1 | 11/2002 | |
| EP | 1676537 A1 | 7/2006 | |
| EP | 1702573 A1 | 9/2006 | |
| EP | 2470085 A1 | 7/2012 | |
| EP | 2484297 A1 | 8/2012 | |
| GB | 2093353 A | 9/1982 | |
| WO | 9215255 A1 | 9/1992 | |
| WO | 9827876 A1 | 7/1998 | |
| WO | 0078236 A1 | 12/2000 | |
| WO | 0105313 A1 | 1/2001 | |
| WO | 2006102124 A2 | 9/2006 | |
| WO | 2013158469 A1 | 10/2013 | |

* cited by examiner

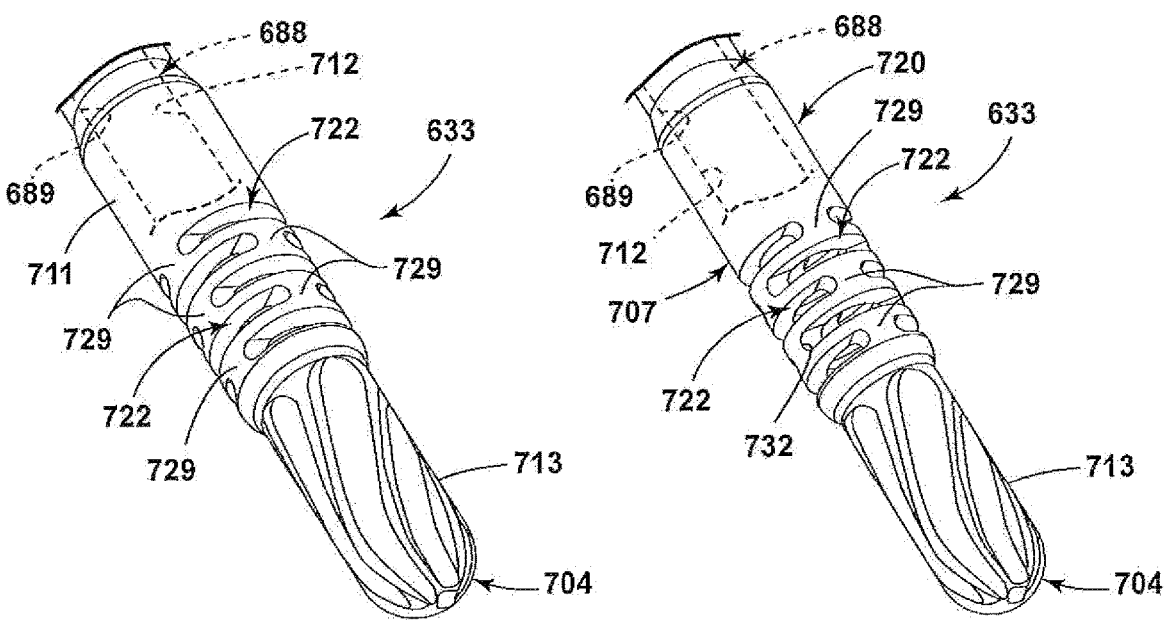
FIG. 16          FIG. 17
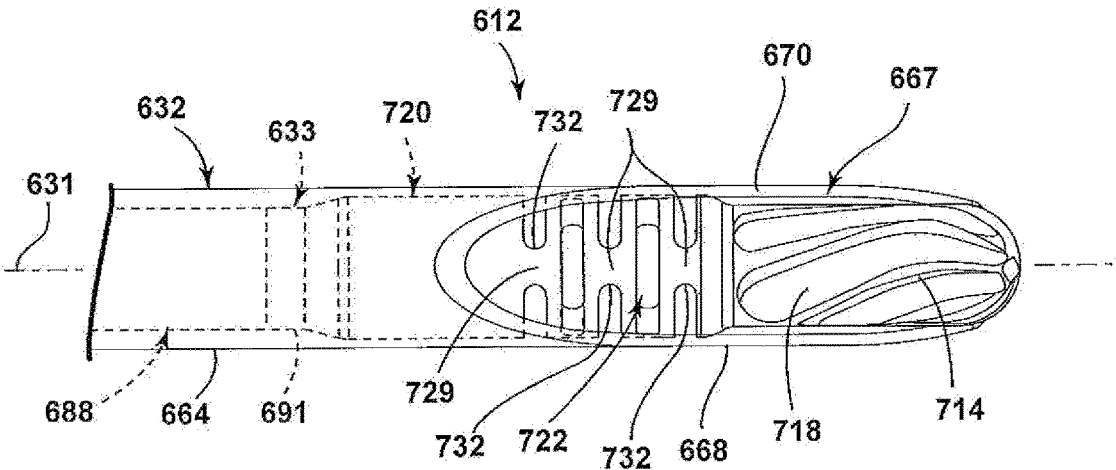
FIG. 18

SURGICAL TOOL ARRANGEMENT AND SURGICAL CUTTING ACCESSORY FOR USE THEREWITH

CROSS-REFERENCE TO RELATED APPLICATIONS

The present application is a continuation of U.S. application Ser. No. 16/593,224, filed Oct. 4, 2019, which is a continuation of U.S. application Ser. No. 14/853,434, filed on Sep. 14, 2015, which claims the benefit of the filing date of U.S. Provisional Patent Application No. 62/064,719, filed Oct. 16, 2014, the disclosures of which are hereby incorporated herein by reference.

FIELD OF THE INVENTION

This invention generally relates to a surgical tool arrangement useful for performing endoscopic surgical procedures which includes a powered handpiece and, more particularly, to a surgical cutting accessory which detachably connects to the handpiece and includes an outer housing element and an inner cutting element with a cutting head for resecting tissue and a suction arrangement at the distal end of the cutting accessory closely adjacent the cutting head which suction arrangement evacuates surgical debris from the surgical site and also operates as a cleaning mechanism for the cutting accessory to prevent buildup of surgical debris adjacent the cutting head. The accessory additionally incorporates a bearing arrangement for supporting the cutting element as same rotates within the housing element.

BACKGROUND OF THE INVENTION

Endoscopic surgical procedures are routinely performed in order to accomplish various surgical tasks. In such a surgical procedure, small incisions or portals are made in the patient. An endoscope, which is a device that allows medical personnel to view the surgical site, is inserted in one of the portals. Surgical instruments used to perform other tasks are inserted into other portals. The surgeon views the surgical site through the endoscope to determine how to manipulate the surgical instruments in order to accomplish the desired procedure. An advantage of performing endoscopic surgery is that, since the portions of the body that are cut open are minimized, the portions of the body that need to heal after the surgery are likewise reduced. Moreover, during an endoscopic surgical procedure, only relatively small portions of the patient's internal organs and tissue are exposed to the open environment. This minimal opening of the patient's body lessens the extent to which the organs and tissue are open to infection.

The ability to perform endoscopic surgery is enhanced by the development of powered surgical tools especially designed to perform such procedures. Once such tool is sold by the assignee hereof under the trademark FORMULA®. This tool is in the form of a cylindrical handpiece designed to be held in the hand of the surgeon. The handpiece has a front or distal end provided with a coupling assembly for releasably holding a cutting accessory, and a motor disposed within a handpiece housing which drives the accessory. The cutting accessories, such as shavers, drills and burs, include an outer housing element having a hub appropriately configured to cooperate with the coupling assembly of the handpiece to lock the accessory thereto and an elongated housing tube having a proximal end fixed to the hub, and an inner cutting element having a drive shaft disposed within the housing tube. When the accessory is attached to the handpiece, the handpiece motor couples to the drive shaft of the accessory and moves same relative to the housing tube. The handpiece motor is selectively actuable to drive the accessory drive shaft so as to cause a desired cutting action at the distal end of the accessory. The handpiece is associated with a control unit which controls the functioning thereof, and is actuated by the user via appropriate buttons provided on the handpiece itself, at the control unit or through use of a footswitch.

In an endoscopic surgical procedure, irrigating fluid is introduced into the surgical site. This fluid serves as a transport media for removing tissue and debris from the surgical site. In order to remove the irrigating fluid and the material contained therein, the above handpiece and the various accessories which are usable therewith together define a suction conduit. A suction pump is connected to the handpiece to provide the suction force needed for drawing the fluid and material away from the surgical site. In order to control the suction flow through the accessory and the handpiece, the handpiece is typically provided with a manually operated valve which is manipulated by the surgeon to control suction of material away from the surgical site.

Mechanical cutting accessories, such as the shaver, drill and bur discussed above, are commonly used in arthroscopic procedures, and allow for the resection of hard and soft bodily tissues, for example, those found within the knee, shoulder and other joints. A bur-type cutting accessory is sometimes used to resect bone or other hard tissues, and includes a cutting head with cutting features which when rotated serve to cut away targeted bone or hard tissue. Such cutting features may include straight or helically-oriented cutting edges which extend longitudinally along the cutting head of the bur. Another bur-type cutting accessory is a diamond bur which includes diamond particles as cutting features which are embedded in a metal surface of the cutting head. Such bur-type cutting accessories often have solid cutting heads so as to have sufficient strength for abrading or cutting hard tissue. A bur-type cutting accessory includes a cutting head with cutting features such as those described above which are exposed through a window formed at the distal end of the outer housing element when the cutting element is located therein. In some bur-type cutting accessories, the window formed in the outer housing element opens primarily sidewardly, so that the distal end of the outer housing element covers a portion or one side of the cutting features of the cutting head of the bur to allow the user to better target bone or hard tissue, and this type of configuration is sometimes referred to as a "hooded" bur. Alternatively, the entire geometry of the cutting head which defines the cutting features may project distally beyond the terminal end of the outer housing element, and this type of arrangement is often called "unhooded". In a bur-type cutting accessory, as contrasted with a surgical shaver, the distal end of the outer housing element typically does not perform any tissue-cutting function, and serves essentially only to house and support the drive shaft of the inner cutting element and to shroud part of the cutting head thereof (in the case of a hooded arrangement), and the cutting of hard tissue is carried out by the cutting features of the cutting head. In an unhooded bur configuration, the outer housing element serves essentially only to house and support the drive shaft. As discussed above, bur-type cutting accessories are typically used for removal of particular bone or hard tissue types, and a variety of different bur geometries are available to specifically address the type of cutting the accessory is to carry out.

Further, in one conventional bur-type cutting accessory, the cutting element includes an elongate and hollow tubular drive shaft and a cutting head with cutting features is provided as a solid member which is fixedly mounted to the distal end of the drive shaft. In order to draw suction through the cutting element in this type of accessory, a suction opening is provided at the distal end of the drive shaft. The suction opening opens sidewardly outwardly and communicates with the hollow interior of the drive shaft, and is located proximally of the cutting features of the cutting head. In operation, bone or other hard tissue removed or cut away by the cutting head is suctioned into the hollow interior of the drive shaft through the window of the outer housing element and the suction opening. In this type of cutting accessory, it is possible that soft tissue can become wrapped around the cutting head in an area just proximal to the cutting features, which can block suction through the suction opening, prevent evacuation of surgical debris, and result in the surgeon's field of view becoming occluded. Such an occurrence will typically require that the surgeon disassemble the cutting accessory and manually unclog the suction opening of the accessory before continuing with the surgery.

Additionally, the various types of surgical cutting accessories as discussed above typically require some type of bearing arrangement which supports the inner cutting element as same rotates within the outer housing element. Such bearing arrangements may include one or more bushings or bearing sleeves provided on the inner cutting element which serve to radially support the inner cutting element within the outer housing element, and a thrust washer or spacer provided at the interface between the mating proximal portions of the inner cutting element and outer housing element which serves to axially support the inner cutting element relative to the outer housing element. In some devices, the bearing sleeve which provides radial support is a heat-shrunk plastic sleeve applied to the exterior of the drive shaft of the inner cutting element. The bushings/bearing sleeves are typically provided as separate components of the accessory, which can complicate assembly/manufacturing. Further, heat-shrunk plastic sleeves have a wide tolerance range, which can make it difficult to maintain the desired gap between relatively movable components.

In an effort to obviate or at least minimize the disadvantages of known surgical accessories, a suction arrangement is provided which can be utilized to both evacuate surgical debris from the surgical site and to provide a self-cleaning function for the cutting accessory. Further, a bearing arrangement provides both radial and axial support for the inner cutting element relative to the outer housing element. The bearing arrangement according to one embodiment is integrated into existing structures of the surgical cutting accessory, and thus provides a simpler and more cost-effective design.

BRIEF DESCRIPTION OF THE DRAWINGS

FIG. 16 is an enlarged and fragmentary perspective view of the distal end of the inner cutting element of a fourth embodiment of the surgical accessory;

FIG. 17 is an enlarged and fragmentary perspective view of the distal end of the inner cutting element of the surgical accessory of the fourth embodiment, with the inner cutting element rotated approximately 90 degrees from the position shown in FIG. 16;

FIG. 18 is an enlarged and fragmentary top view of the distal end of the surgical accessory of the fourth embodiment;

Figure 1:
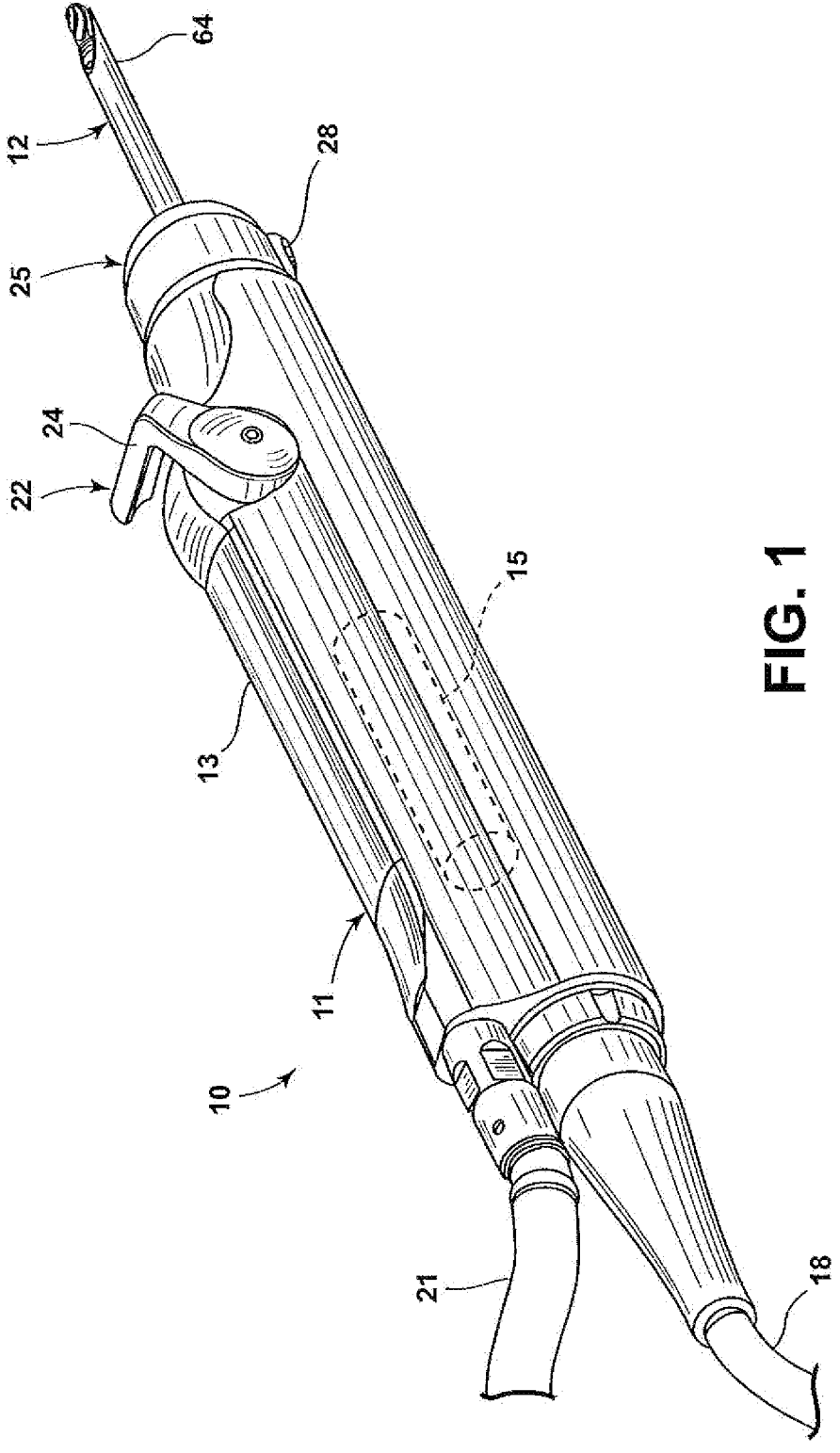
FIG. 1 is a perspective view of the surgical tool arrangement, including a handpiece with a surgical accessory attached thereto.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient or which is first inserted into the patient, and the words "rearwardly" and "proximally" will refer to the direction toward the end of the arrangement which is furthest from the patient. Said terminology will include the words specifically mentioned, derivatives thereof, and words of similar import.

DETAILED DESCRIPTION

Figure 2:
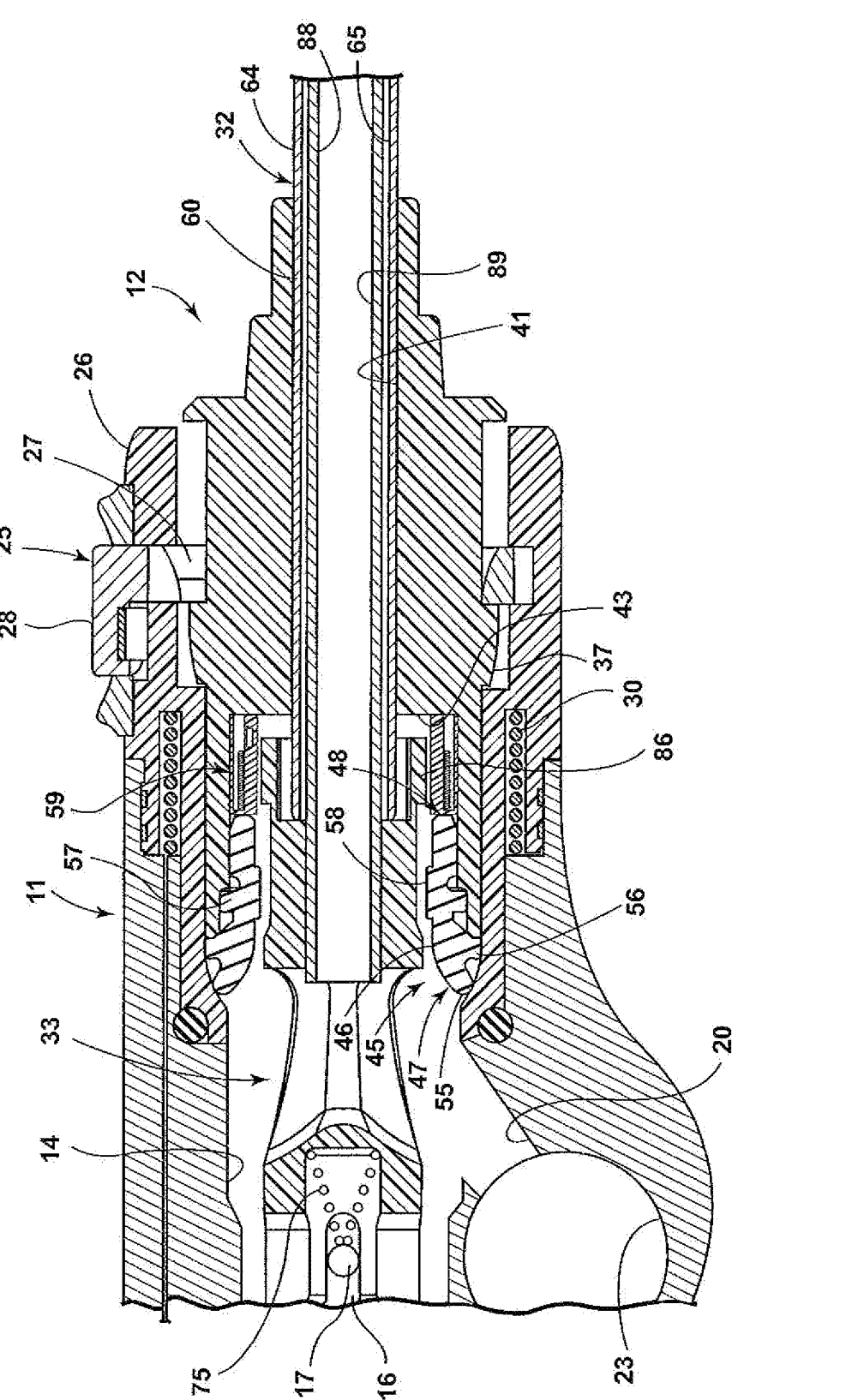
FIG. 2 is an enlarged, fragmentary, longitudinal and cross-sectional view of the handpiece of FIG. 1 with the surgical accessory attached thereto.

Referring to FIGS. 1 and 2, a surgical tool arrangement 10 is illustrated. The arrangement 10 includes a handpiece 11, which at its distal end mounts thereon a surgical accessory 12.

The handpiece 11 is a commercially available surgical handpiece manufactured by the assignee hereof, under Model Nos. 375-704-500 and 375-701-500, and is accordingly only briefly described herein. The handpiece 11 includes an elongate outer housing 13 defining an elongate bore 14 therein. A motor 15 (shown diagrammatically only in FIG. 1) is disposed within the housing bore 14. The motor 15 includes an output or drive shaft 16, which drive shaft 16 mounts a drive pin 17 at the distal end thereof. A power cable 18 is coupled to the proximal end of the handpiece 11 for supplying power to the motor 15.

The handpiece housing 13 defines therein an elongate suction bore (not shown) extending generally parallel to and sidewardly of the housing bore 14. This suction bore communicates with a diagonally extending suction passage 20 defined in the housing 13, which passage 20 provides communication between the distal end of the housing bore 14 and the suction bore. Suction is drawn through the handpiece 11 by a suction pump (not shown), which is connected to the handpiece 11 via a suction tube 21. Suction flow through the handpiece 11 is regulated by an adjustable valve 22 having a valve stem (not shown) which is movably mounted in a valve bore 23 defined in the housing 13. The valve 22 is adjusted by the user via a movable handle or arm 24 connected to the valve stem. The above handpiece suction arrangement is described in detail in U.S. Pat. No. 7,682,333 issued on Mar. 23, 2010, which patent is owned by the same assignee hereof and is hereby incorporated by reference herein in its entirety.

The accessory 12 is removably attached to the distal end of the handpiece 11 by a coupling assembly 25 provided on the handpiece 11. The coupling assembly 25 includes a generally ring-shaped collet 26 secured to the distal end of the handpiece housing 13. A locking ring 27 is movably disposed in the collet 26 and is biased to hold the accessory 12 within the housing bore 14 of the handpiece 11. A release button 28 is provided on the locking ring 27, and is used to release the locking ring 27 and allow removal of the accessory 12 from the handpiece 11. Further, a coil 30 is provided in the collet 26, which is used to facilitate inductive signal transfer to/from a radio-frequency identification device (RFID) disposed in the accessory 12 as discussed below.

Figures 3, 4:
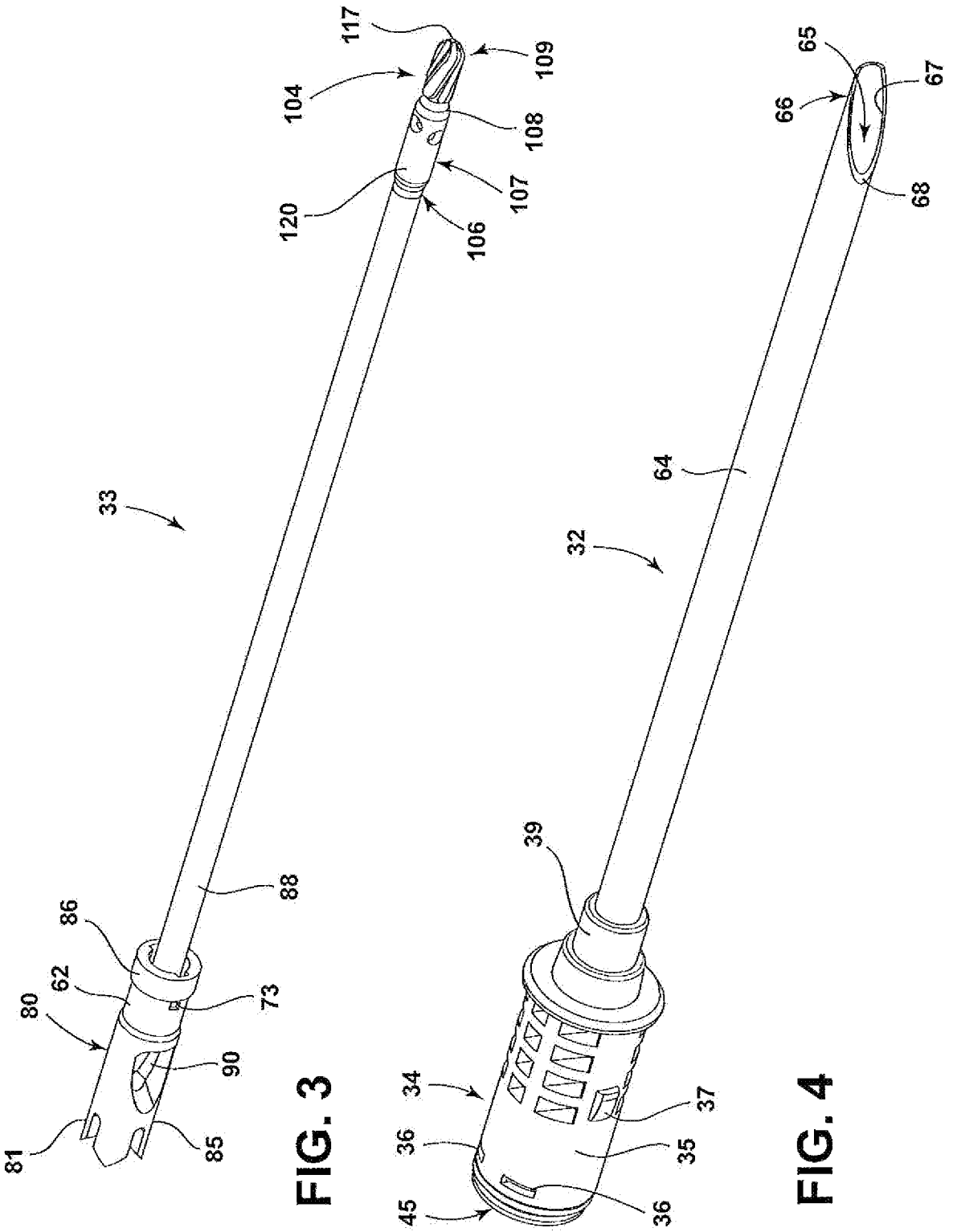
FIG. 3 is a perspective view of the inner cutting element of the surgical accessory.
FIG. 4 is a perspective view of the outer housing element of the surgical accessory.
Figures 7, 8:
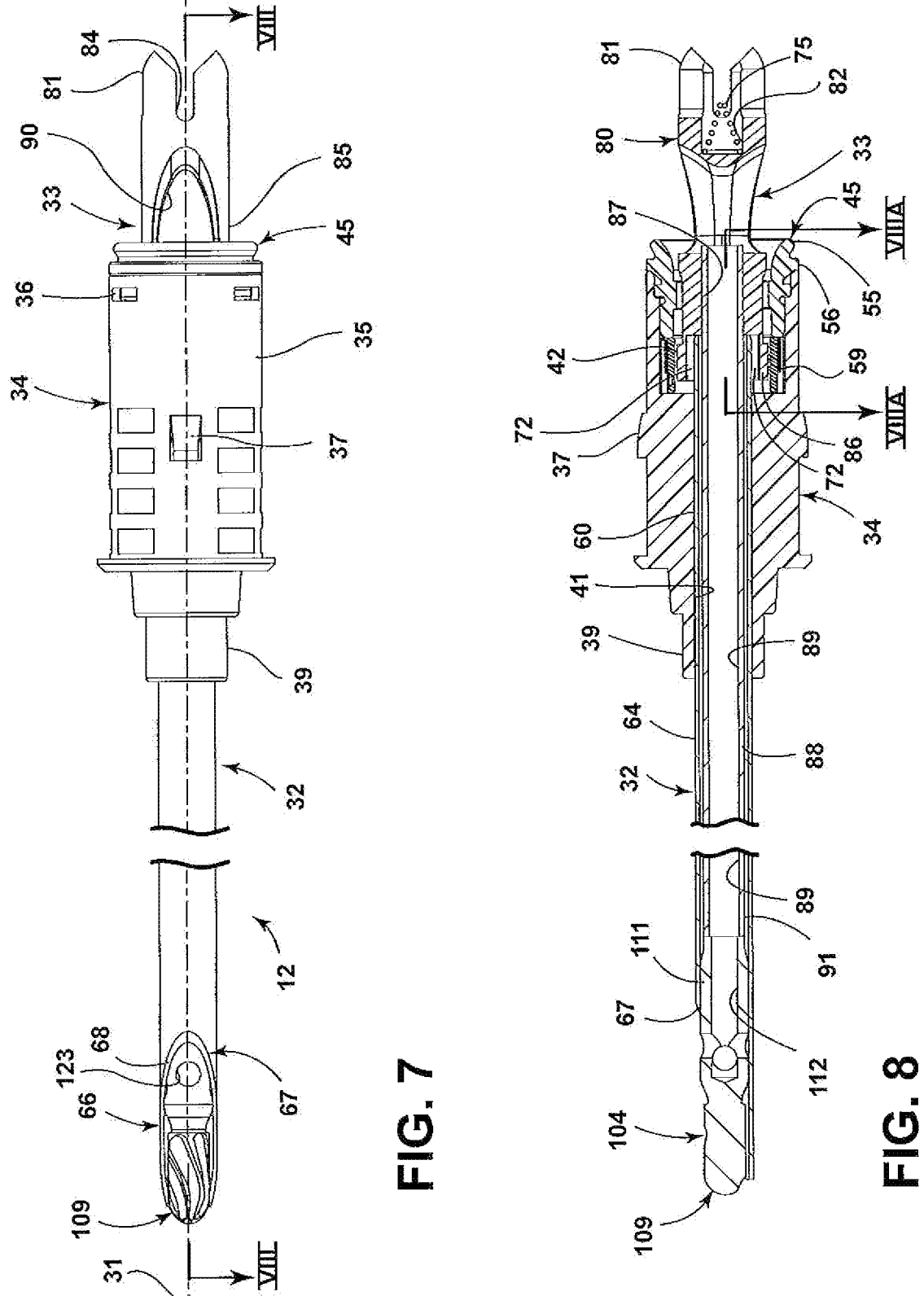
FIG. 7 is an enlarged and fragmentary top view of the surgical accessory.
FIG. 8 is an enlarged longitudinal cross-sectional view of the surgical accessory of FIG. 7, as seen generally along line VIII-VIII in FIG. 7.

Referring to FIGS. 3, 4 and 7-8B, the accessory 12 will now be described. The accessory 12 defines a central longitudinal axis 31, and includes an outer cannula or tubular housing element 32 and an inner tubular cutting element 33 disposed within the housing element 32. The housing element 32 includes a hub 34 which defines the proximal end thereof. The hub 34 is defined by a generally tubular base body 35, which defines therein a plurality of generally rectangular openings 36 adjacent the proximal end thereof which are distributed along the circumference of the hub 34 (only two of which are shown in FIGS. 4 and 7). The base body 35 also has formed thereon a pair of outwardly-projecting, diametrically opposed and generally ramp-shaped ears 37 disposed distally of the openings 36. The ears 37 cooperate with the coupling assembly 25 of the handpiece 11 to secure the accessory 12 therein. The hub 34 has a distal end defined by a head or nose 39 of a reduced diameter as compared to the base body 35. Further, the hub 34 defines therein a bore 41 which opens through a distal end of the hub 34. The bore 41 opens proximally into a counterbore 42 which opens proximally through a terminal end of the base body 35. The bore 41 and counterbore 42 are joined to one another by a shoulder 43 which faces in the proximal direction and extends transversely between the bores 41 and 42. The openings 36 of the base body 35 communicate with bore 42.

Figure 8A:
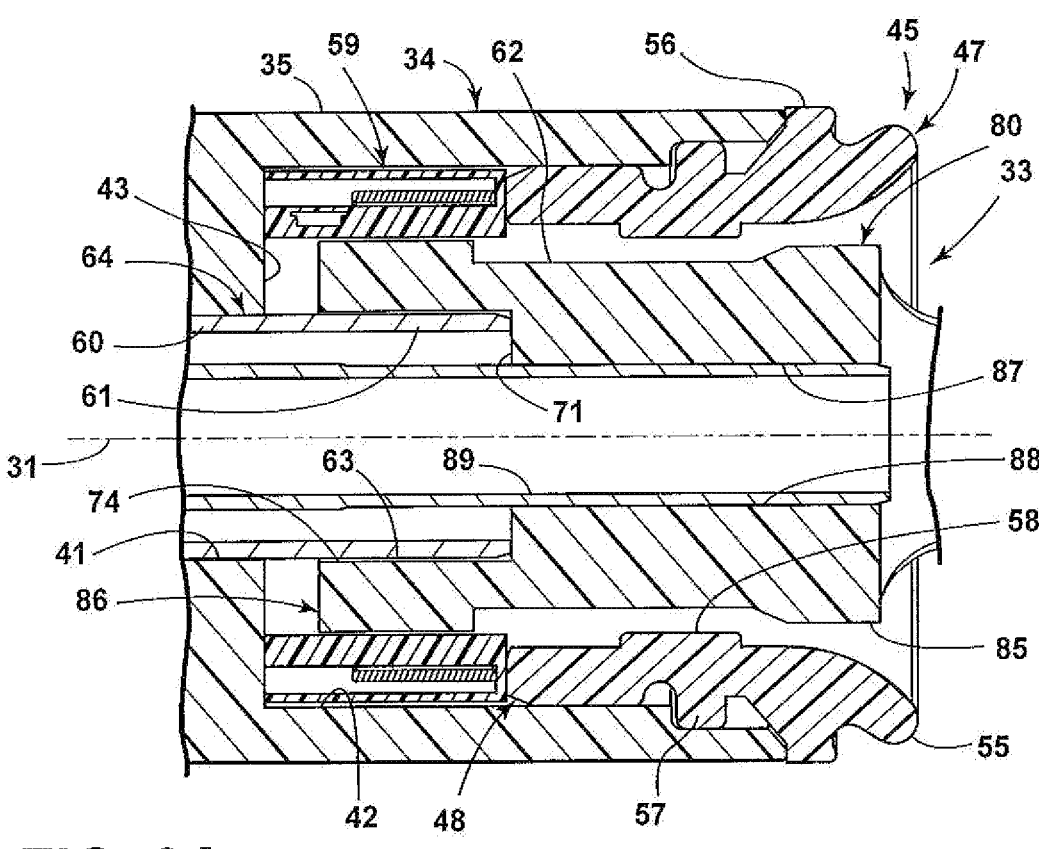
FIG. 8A is an enlarged and fragmentary cross-sectional view of the surgical accessory, as seen generally along line VIIIA-VIIIA in FIG. 8.

An annular seal 45 is disposed within the proximal end of the bore 42 of the hub 34. With reference to FIGS. 2 and 8, the seal 45 is constructed of a resilient elastomeric material, and is defined by a main section 46 and axially-spaced proximal and distal sections 47 and 48 disposed at respective opposite ends of the main section 46. The proximal section 47 defines thereon a pair of annular ribs 55 and 56, which are disposed in sealing engagement with an inner annular surface of the collet 26 of the handpiece 11 when the accessory 12 is coupled thereto, as shown in FIG. 2. The distal section 48 defines thereon a plurality of outwardly projecting and diametrically-opposed lock tabs 57 which engage within the respective openings 36 of the hub 34 to secure the seal 45 to the hub 34 and fix the axial position of the seal 45 relative thereto. The distal section 48 additionally defines thereon a plurality of inwardly projecting and diametrically-opposed stop tabs 58, which are generally radially aligned with the respective lock tabs 57. As shown in FIGS. 2, 8 and 8A, an RFID device 59 encapsulated within a ring structure is located within the hub bore 42 adjacent the distal section 48 of the seal 45.

The above-described coupling arrangement of the handpiece 11 and the arrangement of the encapsulated RFID device 59 and the coil 30 are disclosed in U.S. Pat. No. 7,887,559 issued on Feb. 15, 2011, which patent is owned by the same assignee hereof and is hereby incorporated by reference herein in its entirety.

The outer housing element 32 additionally includes an elongate housing tube 64 which projects distally from the hub 34 (see FIGS. 2, 4 and 7-8A). The housing tube 64 has a proximal end 60 which is fixedly mounted within the bore 41 of the hub 34. The proximal end 60 of the housing tube 64 in the illustrated embodiment is induction bonded to the hub 34 within the bore 41, which hub 34 has a large induction core through which the proximal end 60 extends via bore 41. In this regard, the proximal end 60 of the housing tube 64 may be knurled and/or chamfered so as to facilitate induction bonding of the proximal end 60 to the hub 34. The proximal end 60 extends in the proximal direction axially beyond the shoulder 43 of the hub 34 so as to have an exposed free end 61 which extends into the hub bore 42. The housing tube 64 defines an elongate bore or conduit 65 therein, in which the cutting element 33 is disposed as discussed below. The housing tube 64 has a distal end 66 which in the illustrated embodiment is cut so as to define a window 67 having an annular edge 68, which window 67 in the illustrated embodiment is made via an angled cut, resulting in a window 67 which opens both sidewardly and distally of the tube 64. Alternatively, the distal end 66 of housing tube 64 may be cut in a manner such that the annular edge 68 is oriented perpendicular to the axis 31. Other configurations of the distal end 66 of the housing tube 64 may be provided, and the above are given only by way of example.

Turning now to the cutting element 33 (FIGS. 3 and 7-8B), same includes a hub 80 which defines the proximal end thereof. The hub 80 incorporates a motor-engaging drive element 81 defining a proximally opening bore 82 and slots 84, diametrically aligned pairs of which together define slots which extend transversely to the longitudinal axis 31 of the accessory 12. The hub 80 additionally includes a neck 85 which projects distally from the drive element 81. The neck 85 is joined to an enlarged head 86 by an intermediate section 62. The head 86 defines the terminal distal part of the hub 80. The outer diameter of the head 86 is slightly larger than the inward projection of the respective stop tabs 58 of the seal 45. A proximally oriented bore 87 opens through the proximal end of the hub 80 and extends axially through the neck 85 and a portion of the intermediate section 62, in which is fixed an elongate drive shaft assembly including a drive shaft 88. The drive shaft 88 defines therein a suction passage 89 which is in communication with a pair of suction ports 90 defined in neck 85, which suction ports 90 are in turn in communication with the suction passage 20 of the handpiece 11. In the illustrated embodiment, the suction ports 90 open sidewardly from the hub 80. The proximally-oriented bore 87 opens distally into a counterbore 63 formed in the hub 80 which opens distally through the head 86 thereof. The bore 87 and counterbore 63 are joined to one another by a shoulder 71 which faces in the distal direction and extends transversely to the axis 31 between the bore 87 and the counterbore 63. In the illustrated embodiment, and with reference to FIGS. 8 and 8B, a pair of channels 72 are provided diametrically opposite one another within the counterbore 63 and extend therealong. The channels 72 open radially inwardly and extend longitudinally from the shoulder 71 in the distal direction and open distally through the head 86 of the hub 80. Further, each channel 72 opens radially outwardly via an opening 73 which extends completely through the wall of the intermediate section 62 of the hub 80.

With reference to FIGS. 3, 5, 6 and 8, the drive shaft assembly includes a cutting head 104. In the illustrated embodiment, the drive shaft 88 and the cutting head 104 of the drive shaft assembly are constructed as separate components which are fixed to one another. In this regard, the drive shaft 88 may be constructed of a rigid plastic and a distal end 91 thereof induction welded to the cutting head 104, which may be constructed of rigid metal, such as stainless steel. Alternatively, the drive shaft 88 and the cutting head 104 may be constructed as an integral or one-piece member formed from rigid metal, such as stainless steel. The cutting head 104 is generally cylindrical and partially tubular in the illustrated embodiment as discussed below.

Figure 5:
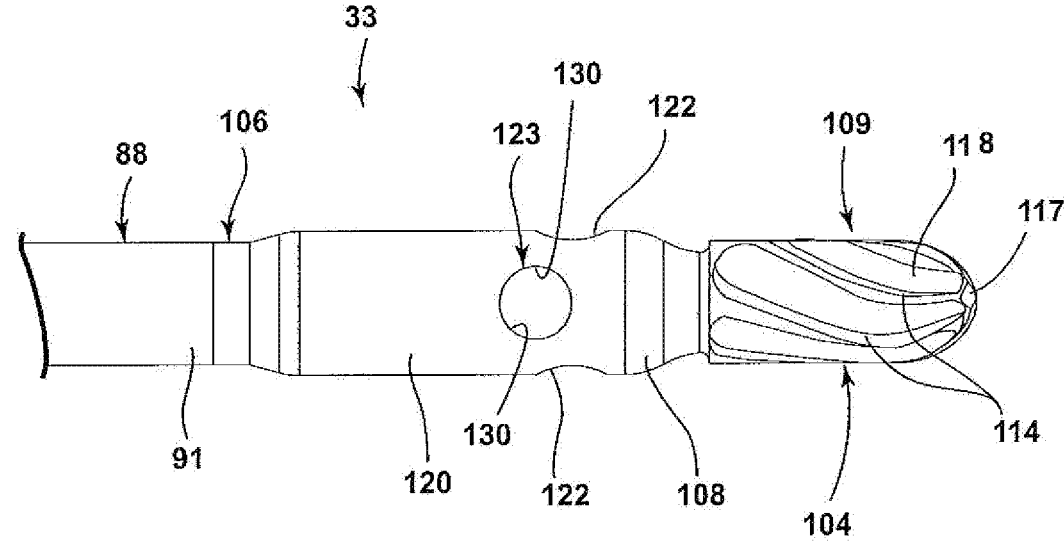
FIG. 5 is an enlarged and fragmentary top view of the distal end of the inner cutting element.
Figure 6:
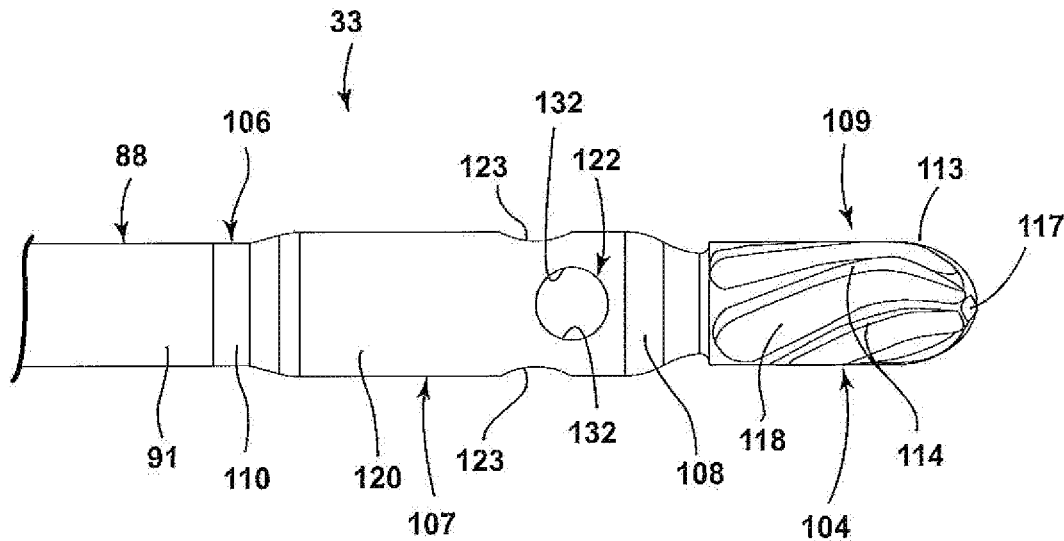
FIG. 6 is an enlarged and fragmentary view of the distal end of the inner cutting element rotated approximately 90 degrees from the position shown in FIG. 5.
Figure 10:
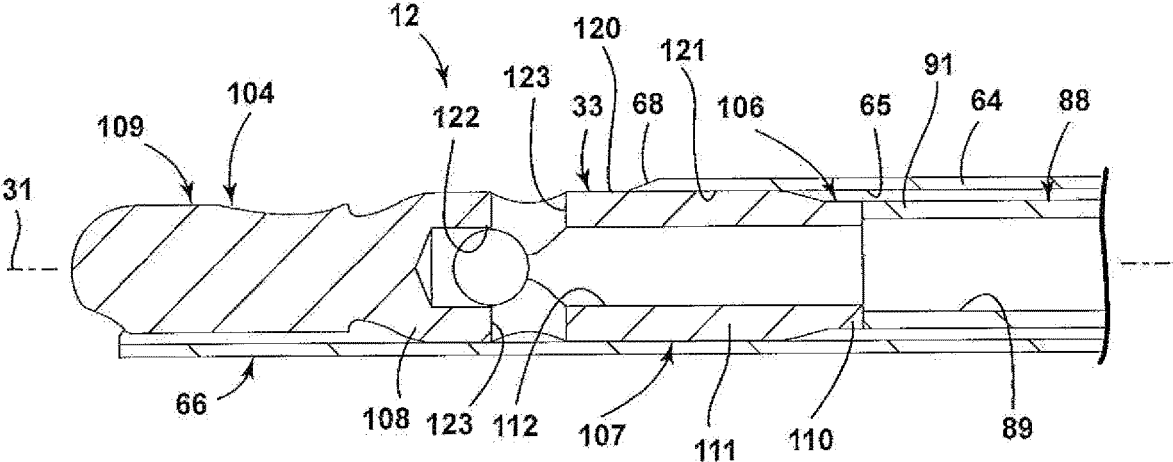
FIG. 10 is an enlarged cross-sectional view of the surgical accessory, as seen generally along line X-X in FIG. 9.

As best shown in FIGS. 5, 6 and 10, the cutting head 104 includes a tubular proximal end 106 of a generally constant diameter and which in the illustrated embodiment is fixed to the distal end 91 of the drive shaft 88, a tubular neck portion 107 extending distally from the proximal end 106 and a distal end 109 which extends distally from a conical distal end 108 of the neck portion 107. The majority of the neck portion 107 has an enlarged outer diameter as compared to the outer diameter of the proximal end 106. Where the neck portion 107 adjoins the proximal end 106, the neck portion 107 tapers gradually outwardly away from the axis 31 of the surgical accessory 12 as the neck portion 107 projects away from the proximal end 106. The proximal end 106 and the neck portion 107 are each defined by respective walls 110 and 111, the inner surfaces of which walls 110, 111 together define a suction passage 112 which extends proximally from the distal end 109 of the cutting head 104 and opens through the proximal end 106 for communication with the suction passage 89 of the drive shaft 88.

The distal end 109 of the cutting head 104 is configured for cutting bodily tissue and has a configuration of what is commonly considered a bur. The distal end 109 is generally cylindrical and defines an exterior surface 113 having formed thereon a plurality of cutting features, such as cutting edges 114. In the illustrated embodiment, and as shown in FIGS. 8 and 10, the distal end 109 is a solid member. The cutting edges 114 project outwardly from the exterior surface 113 in a direction away from the axis 31, and in the illustrated embodiment additionally extend in a helical manner about the axis 31 along the longitudinal extent of the distal end 109 and in a generally parallel manner with one another along a majority of the longitudinal extent of the distal end 109. The cutting edges 114 extend gradually towards one another in the proximal to distal direction and terminate adjacent a tip 117 of the distal end 109. A flute or groove 118 is defined between each adjacent pair of cutting edges 114, which grooves 118 extend helically about the axis 31 along the distal end 109. It will be appreciated that the cutting edges 114 may alternatively be non-helical or substantially straight so as to extend generally parallel with the axis 31 or so as to be oriented at an angle relative to the axis 31. The respective grooves/flutes 118 in this embodiment would thus also be substantially straight. Further, the number of cutting edges 114 will vary depending upon the dimensions of the cutting head 104 and/or the type of cutting action desired, and the configuration of the cutting edges 114 as disclosed herein is presented only as an example of one suitable configuration for cutting edges of a cutting head 104.

Figure 9:
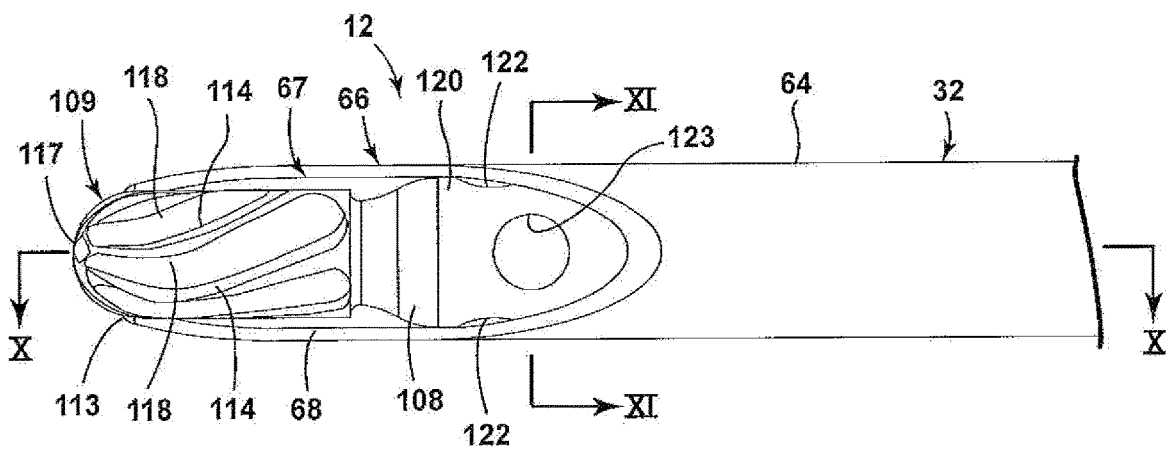
FIG. 9 is an enlarged and fragmentary top view of the distal end of the surgical accessory.

Referring to FIGS. 9 and 10, the wall 111 of the tubular neck portion 107 has an outer surface 120 with an outer diameter which is greater than an outer diameter of the distal end or bur 109 and slightly smaller than the inner diameter of the housing tube 64. Further, the configuration or contour of the outer surface 120 is similar to or substantially conforms to the contour of an inner surface 121 of the housing tube 64. The outer surface 120 thus serves as a bearing surface via its engagement with the inner surface 121 of the housing tube 64. The cooperation between the inner surface 121 and the outer surface 120 forms a distal bearing for rotatably supporting the drive shaft 88 within the housing tube at the distal end of the surgical accessory 12.

The wall 111 of the tubular neck portion 107 defines a suction opening therein which opens outwardly through the bearing surface 120, and in the illustrated embodiment, a plurality of such suction openings 122 and 123 are provided within the wall 111 which open outwardly through the bearing surface 120. The suction openings 122 and 123 are oriented in circumferentially spaced-apart relation with one another about the neck portion 107. In the illustrated embodiment, the suction openings 122 and 123 are spaced at approximately 90 degree intervals from one another along the circumference of the neck portion 107, and two of the suction openings 122 are located diametrically opposite one another (approximately 180 degrees from one another), are axially aligned with one another, and are located closer to the distal end or bur 109 than the remaining two suction openings 123. The remaining two suction openings 123, or proximal suction openings 123, are axially aligned with one another and are diametrically opposite one another on the neck portion 107. Each of the suction openings 122 and 123 extends completely through the wall 111 for communication with the suction passage 112 of the cutting head 104 and the suction passage 89 of the drive shaft 88, and in the illustrated embodiment each suction opening 122, 123 has a circular configuration.

Figure 11:
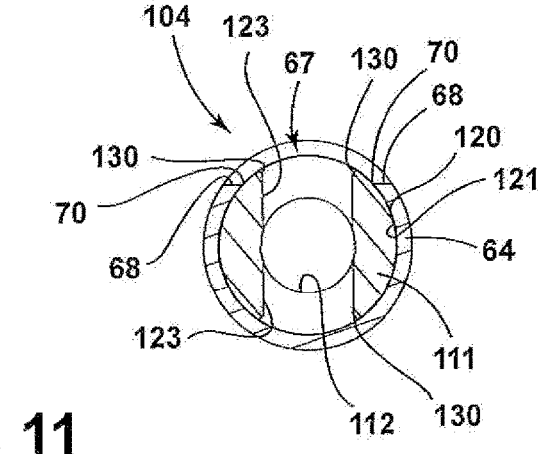
FIG. 11 is an enlarged cross-sectional view of the surgical accessory as seen generally along line XI-XI in FIG. 9.

As best shown in FIGS. 10 and 11, the placement of the suction openings 122 and 123 in the bearing surface 120 positions the openings 122 and 123 in close, face-to-face or opposed relationship (in a radial direction relative to the axis 31) with the inner surface 121 of the housing tube 64. Further, each of the suction openings 122 and 123 has a pair of opposed edges 132 and 130 (see FIGS. 5, 6 and 11) adjacent the bearing surface 120 of the neck portion 107 which edges, when the inner cutting element 33 is rotated inside the outer housing element 32, are positioned in circumferentially opposed relation with the adjacent edge 68 of the housing element window 67 as discussed further below. These edges 130 and 132 can be provided with a blunt or non-acute configuration, a chamfered edge configuration suitable for non-aggressive cutting or resection of tissue such as the edge configuration shown in FIG. 11, or a sharp or acute edge configuration suitable for more aggressive cutting of tissue.

The inner cutting element 33 is assembled to the outer tubular housing element 32 by inserting the distal end 109 of the cutting element 33 into the proximal end of the bore 42 of the hub 34. During this insertion, the enlarged head 86 of the hub 80 expands the seal 45 and the head 86 pushes past the stop tabs 58, at which point the seal 45 essentially resumes its original shape. The stop tabs 58, while allowing some axial displacement of the cutting element 33 relative to housing element 32, prevent the cutting element 33 from detaching or falling out of the housing element 32 due to gravitational forces. When the cutting element 33 is fully inserted into the housing element 32, the free end 61 of the housing tube 64 extends in the proximal direction into the counterbore 63 of the hub 80 and abuts against the shoulder 71, as best shown in FIG. 8A. The wall of the hub 80 which defines the counterbore 63 has an inner surface 74 with a diameter which is similar to, but slightly larger than, the outer diameter of the free end 61 of the housing tube 64, such that there is only a small radial clearance between the free end 61 and the inner surface 74. The engagement of the outer surface of the free end 61 of the housing tube 64 with the inner surface 74, and the abutting engagement of the free end 61 of the housing tube 64 with the shoulder 71, provides a radial bearing and an axial bearing, respectively, at the proximal end of the surgical accessory 12. As discussed further below, when the accessory 12 is mounted to the handpiece 11, a spring 75 provided within the drive element 81 of the cutting element 33 cooperates with the handpiece 11 and biases the cutting element 33 axially in the distal direction relative to the outer housing element 32, which serves to maintain the free or terminal end 61 of the housing tube 64 axially against the shoulder 71.

Figure 8B:
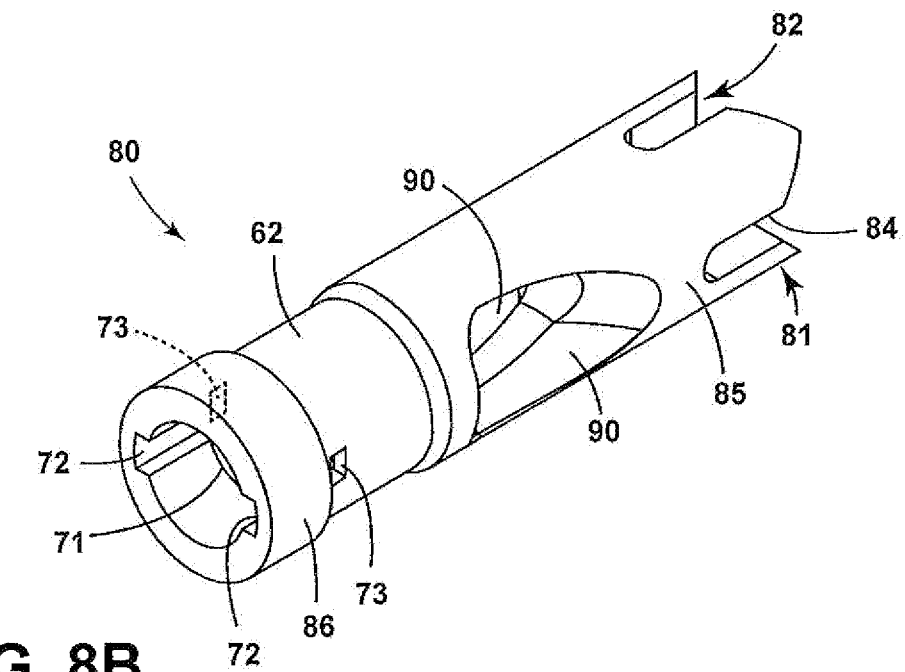
FIG. 8B is an enlarged perspective view of the hub of the inner cutting element in isolation.

The mating areas between the inner surface 74 of the hub 80 and the outer surface of the free end 61 of the housing tube 64 can be provided with lubricant in order to minimize friction between these components during movement of the inner cutting element 33 relative to the outer housing element 32. In this regard, and as best shown in FIGS. 8 and 8B, lubricant can be applied to the counterbore 63 through the openings 73 and/or through the distally opening areas of the channels 72, so that the lubricant will enter the channels 72 and lubricate between the free end 61 of the housing tube 64 and the hub 80.

The assembled accessory 12 is secured to the handpiece 11 in a similar manner to that described in the '559 patent referenced above, and this assembly will accordingly be only briefly described here. The accessory 12 is attached to handpiece 11 by inserting the hubs 34 and 80 into the open distal end of the collet 26. The ears 37 of the hub 34 seat within the collet 26, and the locking ring 27 serves to hold the accessory 12 within the handpiece 11. The above securement of the accessory 12 to the handpiece 11 causes the drive element 81 of the accessory 12 to engage the motor output shaft 16 of the handpiece 11. More specifically, the drive pin 17 of the output shaft 16 seats within the aligned slots 84 of the drive element 81, such that the rotational movement of the output shaft 16 is transferred to the cutting element 33. Further, the drive pin 17 engages the spring 75 so as to axially bias the cutting element 33 in the distal direction.

In operation, the distal end of the tool 10 is inserted into the surgical site. The cutting element 33 is controlled by a control unit (not shown) connected to the handpiece cable 18, which control unit supplies electrical power to the motor 15 of the handpiece 11 in order to actuate the cutting element 33 and control the rotational speed thereof. If cutting of tissue is desired, then the motor 15 is activated so as to cause the cutting element 33 to rotate within and relative to the outer housing element 32, which effectively rotates the cutting head 104 to allow the removal of tissue at the surgical site. In this regard, it will be appreciated that the control unit may include appropriate control buttons so as to allow the surgeon or operator to select the desired accessory operations. These control functions of the cutting element 33 may alternatively be performed directly from the handpiece 11 which would then include the appropriate control buttons thereon. Alternatively, the control unit may be associated with a switch, either through a suitable cable or wirelessly, to allow the surgeon to operate the controls remotely. Such a switch may be a footswitch or a hand switch.

As shown in FIGS. 9 and 10, with the cutting element 33 disposed within the housing element 32 and the accessory 12 secured to handpiece 11 as described above, the cutting head 104 is positioned adjacent the window 67 of the housing element 32 so that at least a portion of the cutting head 104 is exposed. In this regard, the cutting features of the cutting head 104 are shown herein as being covered on one side thereof by the distal end 66 of the housing element 32. However, it will be appreciated that other configurations of the housing element distal end 66 may be provided. For example, the housing tube 64 of the housing element 32 may be provided with a length which allows full exposure of the cutting features of the cutting head 104 axially beyond the distal end 66 of the housing tube 64, so that the cutting features of the cutting head 104 are unhooded or uncovered completely.

The annular edge 68 of the housing tube 64, as shown in FIG. 11, is shaped so as to have a pair of opposed edges 70 which, when the cutting element 33 is assembled to the housing element 32 and is rotated relative thereto, act to clear surgical debris from the suction openings 122 and 123 as discussed further below. The edges 70 may be provided with a blunt or non-acute configuration, a chamfered configuration suitable for cutting or resecting tissue, or a sharp or acute configuration suitable for more aggressive tissue cutting.

If desirable or necessary, suction can be provided at the surgical site by manipulating the valve 22 on the handpiece 11 to draw surgical debris from the surgical site, first through the window 67 of the housing element 32 and then through the suction openings 122 and 123. In this regard, the axial location of the suction openings 122 and 123 along the neck portion 107, the size of the window 67 of the housing element 32 and the distribution of the suction openings 122 and 123 about the neck portion 107 can be configured so that at least one of the suction openings 122 or 123 is located within the window 67 essentially at all times during rotation of the cutting element 33 relative to the housing element 32. Surgical debris resulting from the cutting action of the cutting head 104 can be suctioned into the window 67 of the housing element 32 and into an exposed suction opening 122 and/or 123, which debris is then suctioned into the suction passage 112 of the cutting head 104, into the drive shaft suction passage 89, into the handpiece suction passage 20 and proximally through the handpiece 11 towards the suction pump. The positioning of the suction openings 122 and 123 for communication with the window 67 and immediately proximate to the cutting features 114 of the cutting head 104 enables quick evacuation of the surgical debris from the surgical site.

In conventional cutting accessories, it is common for soft tissue to become wrapped around the cutting features, or an area just proximal thereof, during a surgical procedure, which in turn can cause clogging of the suction opening located proximal to the cutting features as discussed above. However, because the suction openings 122 and 123 open outwardly through the bearing surface 120 and the bearing surface 120 is radially spaced from the inner surface 121 of the housing tube 64 by a relatively small amount, soft tissue is prevented from wrapping around the distal end 109 of the accessory 12 and clogging the suction openings 122 and 123. Further, when the cutting element 33 is rotated within and relative to the housing element 32, any tissue which is lodged or entangled within or adjacent the suction openings 122, 123 will be wiped away or dislodged by the edge 70 of the window 67 of the outer housing element 32 as the edge 132 or 130 of the suction opening 122 or 123 rotates towards or approaches the adjacent edge 70 of the housing window 67. When the inner cutting element 33 is rotated within and relative to the outer housing element 32, the suction opening 123 (or the suction opening 122) moves towards the stationary edge 70 of the window 67 of the outer housing tube 64. When the suction opening 123 (or the suction opening 122) meets and moves past the edge 70, a wiping or cleaning action will take place which, due to the close proximity (in the radial direction) of the edge 70 to the suction opening, will serve to clear any accumulated tissue from the suction opening.

As discussed above, the edges 132 and 130 of the inner cutting element 33 and/or the edges 70 of the outer housing element 32 may be configured as cutting edges, which, in addition to the wiping action described above, provides a resection or cutting action at the suction openings 122 and 123. Should tissue become lodged adjacent the window 67 during a procedure, according to this embodiment, the tissue will be resected between the respective edge 130, 132 of the suction opening 122 or 123 and the edge 70 of the window 67 of the outer housing element 32, which edges together create a scissoring action when the cutting element 33 is rotated relative to and within the housing element 32. More specifically, any tissue which is lodged within or adjacent the suction opening 122 or 123 will be caught by the edge 132 or 130 of the suction opening 122, 123 as same rotates towards the adjacent edge 70 of the housing window 67, which effectively will server the tissue between the two edges (132 and 70, 130 and 70) and allow suction of the resected tissue away from the surgical site.

The arrangement of the suction openings 122 and 123 on the bearing surface 120 of the cutting head 104 can thus prevent, or at least minimize, occlusion of the surgeon's field of view by surgical debris due to the wiping action performed by the edges 70 of the window 67 of the outer housing element 32 over the suction openings 122 and 123 as same rotate towards and past the adjacent edge 70 of the housing window 67. Further, if the edges 130, 132 and/or 70 are configured as cutting edges, tissue resection can additionally be carried out. This arrangement will prevent the surgeon from having to dismantle the surgical accessory 12 from the handpiece 11 and remove the cutting element 33 from the housing element 32 in order to remove the tissue causing the clog.

The window 67 of the outer housing tube 64 is sized, and the suction openings 122 and 123 are disposed in appropriate axial positions along the cutting head 104 of the drive shaft 88, so that the suction openings 122, 123 are exposed (i.e. unblocked by the distal end 66 of the housing tube 64) through the housing window 67 along with at least a portion of the cutting head 104. In this regard, the suction openings 122, 123 will be exposed to the surgical site through the window 67 when the suction openings 122, 123 are rotationally aligned with the window 67, and in the illustrated embodiment at least two suction windows 122, 123 will be at least partially exposed at one time during rotation of the drive shaft 88. This arrangement allows the evacuation of surgical debris through the window 67 directly into the suction openings 122, 123.

Further, the suction openings 122, 123 are provided as separate structures from the cutting head 104. That is, the suction openings 122, 123 are not provided or defined in the cutting head 104, for example, between the cutting edges 114 or otherwise directly on the cutting head 104. This arrangement is easier to manufacture and also allows the cutting head 104 to have a structure, when necessary or desirable, which is sufficiently rigid to withstand aggressive cutting. While the suction openings 122, 123 are separate structures from the cutting head 104, the suction openings 122, 123 are nonetheless positioned very close (in the axial direction) to the cutting head 104 which results in more immediate suctioning and thus removal of surgical debris. Additionally, the wiping action of the edges 70 of the outer housing element window 67 over the suction openings 122, 123 provides an efficient anti-clogging/cleaning mechanism. Also, in the embodiment wherein the suction opening edges 130 and 132 and/or the edges 70 of the housing element window 67 are configured as cutting edges, the scissoring action between the edges 130, 132 and the edges 70 allow for tissue resection adjacent the window 70. Further, providing suction openings 122, 123 at varying axial locations along the bearing surface 120 allows suction, and in the embodiment where the edges 130, 132 and/or edges 70 are configured as cutting edges, a cutting action, over an increased area (in the axial direction) along the bearing surface 120. In some conventional burr-type surgical accessories, the size of the suction openings or windows are necessarily made large in an attempt to prevent clogging thereof. These large-size suction openings or windows can cause the accessory to use a large amount of saline or irrigating fluid during surgery and thus can result in a high flow-rate. Since these accessories can extract more saline than the inflow pump can provide, the pressure at the surgical site (such as in a bodily joint) can fall and potentially cause joint collapse. For this reason, surgeons often keep the suction function of the accessory turned off and only occasionally turn same on to clear the field of view at the surgical site. The suction openings 122 and 123 can be made much smaller as compared to conventional accessories (in some cases 70% smaller than a conventional burr-type cutting accessory), due to the cooperation between the suction openings 122, 123 and the housing window 67 as discussed herein, which provides an efficient cleaning mechanism for the suction openings 122, 123. The smaller size of the suction openings 122, 123 results in reduced saline consumption and accordingly reduces the possibility of joint collapse during surgery. Further, the surgeon is able to utilize and/or maintain suction through the accessory 12 during a cutting operation which will provide a better field of view of the surgical site during a cutting operation.

The bearing arrangement described herein includes the distal bearing defined by the outer surface 120 of the inner cutting element 32 which engages with the inner surface 121 of the housing tube 64 of the outer housing element 32, and the proximal bearing defined by the engagement of the outer surface of the free end 61 of the housing tube 64 with the inner surface 74 of the hub 80 and the engagement of the terminal end 61 of the housing tube 64 with the shoulder 71. With respect to the proximal bearing, the increased depth (in the axial direction) at which the housing tube 64 is bonded to the hub 34 of the housing element 32, resulting in the extension of the terminal end 61 of the housing tube 64 into the bore 42 and beyond the shoulder 43, allows coupling or attachment of the hub 80 of the cutting element 33 to this terminal end 61. This arrangement in effect allows the use of existing components, namely the housing tube 64 and the hub 80, to provide a proximal bearing site, and the drive shaft 88/cutting head 104 and the inner surface 121 of the housing tube 64 to provide a distal bearing site, and thus provides bearings for the inner cutting element 33 at axially opposite ends of a very stiff housing tube 64. Due to the increased depth at which the housing tube 64 extends into the hub 34, the stiff housing tube 64 and the handpiece 11 overlap at the connection point between the two, i.e. adjacent the collet 26. This means that the tool 10 is stiff all of the way from the handpiece 11 to the distal end 109 of the accessory 12, with very little stiffness lost at the connection between the handpiece 11 and the accessory 12 at the collet 26, which provides a more rigid and stable tool 10. Further, the utilization of the hub 80 of the cutting element 33 and the free end 61 of the housing tube 64 as both an axial and radial bearing lends stability to the accessory 12 at the proximal end thereof and ensures that a radial gap is maintained between the drive shaft 88 and the housing tube 64 at the proximal end of the accessory 12. In some conventional arrangements, a metal or low-friction plastic spacer is used as an axial bearing between the rotating hub of the inner cutting element and the hub of the outer housing element. Thus, the utilization of existing components of the accessory 12 to provide both axial and radial bearing support provides a simpler and more cost efficient arrangement.

In one embodiment, the wall 111 of the neck portion 107 of the cutting head 104 (which defines the outer surface 120) and the housing tube 64 may be constructed of stainless steel coated with a low-friction and wear resistant material. This construction reduces wear during surgery which in turn reduces particle generation at the surgical site, and provides hard, low-friction and corrosion-resistant surfaces. Some conventional surgical accessories utilize a metal-on-metal bearing arrangement at the distal end of the accessory wherein at least one of the bearing components is a separate component. Providing a bearing as a separate component is necessarily more difficult and expensive to manufacture. In contrast, the distal bearing arrangement is integrated into existing components, resulting in a less expensive and simpler arrangement.

The cutting head 104, in the illustrated embodiment, can be provided as an integral structure which is machined from a single stainless steel bar stock to form the cutting edges 114, a larger diameter portion (the neck portion 107) proximal to the cutting edges 114 on which the outer (bearing) surface 120 is formed and the suction openings 122 and 123. The drive shaft 89 can be constructed of plastic and induction bonded to the cutting head 104.

Utilizing a metal bearing surface, such as the surface 120 of the cutting head 104, which is machined during formation of the cutting head 104, provides a repeatable and very stable bearing surface in close proximity to the cutting features 114 of the cutting head 104. This surface 120 can be machined to very tight tolerances such that the gap between the outer diameter of the bearing surface 120 and the inner diameter of the adjacent portion of the housing tube 64 can be kept very small and is easily repeatable during manufacture, meaning that the gap between the cutting edges 114 and the hood created by the distal end 66 of the housing tube 64 (when the bur is of a hooded-type as in the illustrated embodiment), is repeatable. As a result of this repeatability in gap size between components, as well as the stable bearing arrangement in close proximity (in the axial direction) to the cutting features 114 of the cutting head 104, the accessory 12 is able to withstand significantly more force (sideload) before the cutting features 114 will collide or make contact with the distal end 66 of the housing tube 64, which can potentially cause metal debris to be generated at the surgical site. The stable and low-friction bearing arrangement also means the accessory 12 is able to withstand significantly more force (sideload) before the drive shaft 88 makes contact with the housing tube 64, which can potentially cause stalling out or failure of the accessory.

FIGS. 12-21 illustrate additional embodiments of the surgical accessory 12 which are substantially identical to the first embodiment of the surgical accessory 33, except that these embodiments incorporate alternative configurations or geometries of the suction openings provided in the bearing surface of the inner cutting element of the surgical accessory 12 as discussed below.

Figure 12:
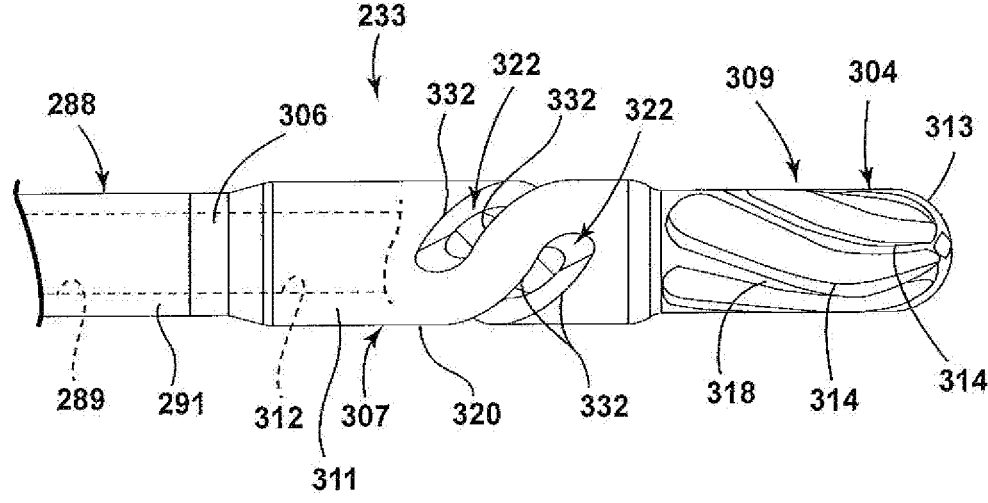
FIG. 12 is an enlarged and fragmentary top view of the distal end of the inner cutting element of a second embodiment of the surgical accessory.
Figure 13:
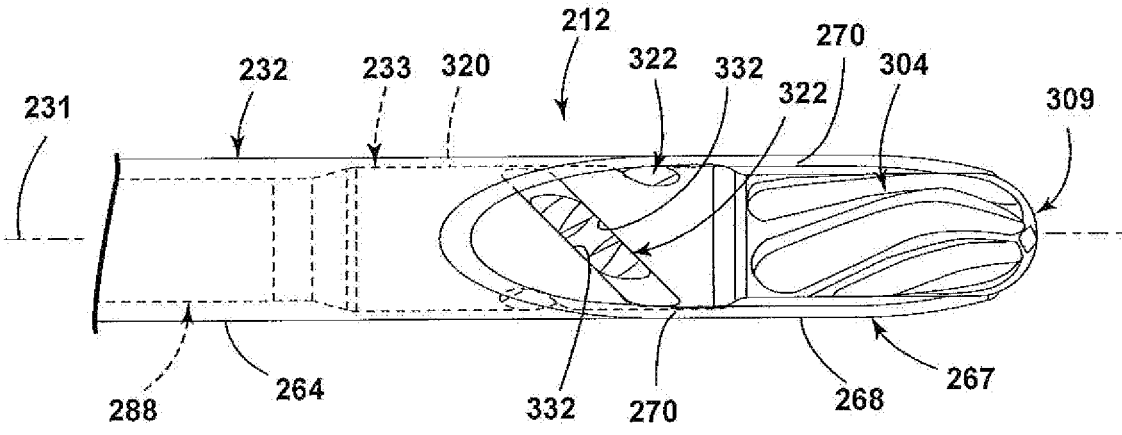
FIG. 13 is an enlarged and fragmentary view of the distal end of the surgical accessory of the second embodiment with the inner cutting element rotated approximately 180 degrees from the position shown in FIG. 12.

FIGS. 12 and 13 illustrate a second embodiment of the surgical accessory. Components of the second embodiment which are similar or identical to components of the first embodiment of the surgical accessory 12 will include the same reference numbers as in the prior embodiment, plus "200", and a detailed description of all components will accordingly not be provided. The surgical accessory 212 according to the second embodiment includes an inner cutting element 233 rotatably disposed within an outer housing element 232. The inner cutting element 233 incorporates a drive shaft assembly including a drive shaft 288 having a distal end 291 with a cutting head 304. The tubular neck portion 307 of the cutting head 304 defines therein a plurality, and here three, of suction openings 322 which open outwardly through the bearing surface 320 of the neck portion 307. These suction openings 322 are substantially identical to one another and each has an elongated configuration and extends in a helical manner about the longitudinal axis 231 of the accessory 212 as the opening 322 projects longitudinally along the bearing surface 320. In the illustrated embodiment, the suction openings 322 are uniformly circumferentially spaced from one another about the neck portion 307. Each of the suction openings 322 extends completely through the wall 311 for communication with the suction passage 312 of the cutting head 304 and the suction passage 289 of the drive shaft 288. Each of the suction openings 322 has a pair of opposed edges 332 disposed at the bearing surface 320.

The inner cutting element 233 is housed within the outer tubular housing element 232 and the assembled accessory 212 is secured to the handpiece 11 as in the prior embodiment. As shown in FIG. 13, with the cutting element 233 disposed within the outer housing element 232, the cutting head 304 and the bearing surface 320 are positioned adjacent the window 267 of the housing element 232 so that at least a portion of the cutting head 304 and one or more of the suction windows 322 are exposed through the window 267. Further, with the cutting element 233 assembled to the housing element 232, during use, the edges 270 of the housing tube 264 act to wipe debris away from the suction openings 322 as the inner cutting element 233 rotates within the outer housing element 232, as in the prior embodiment. The edges 332 of the suction windows 322 and/or the edges 270 of the housing tube 264 may be provided with edges suitable for cutting/resecting tissue. In this embodiment, the cutting edges 332 of the suction windows 322 cooperate with the edges 270 of the housing tube 264 to cut or resect tissue as the cutting element 233 rotates within the housing element 232 should this be necessary due to a buildup of surgical debris.

Figure 14:
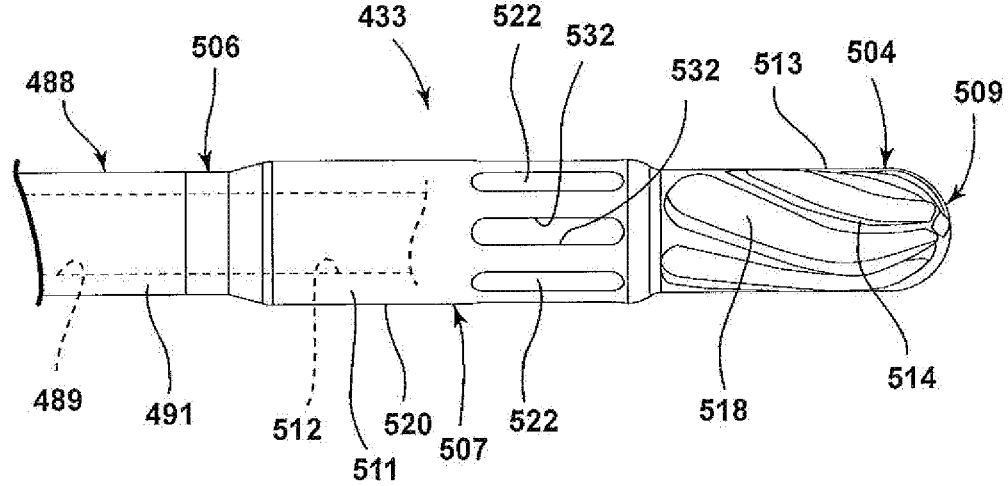
FIG. 14 is an enlarged and fragmentary top view of the distal end of the inner cutting element of a third embodiment of the surgical accessory.
Figure 15:
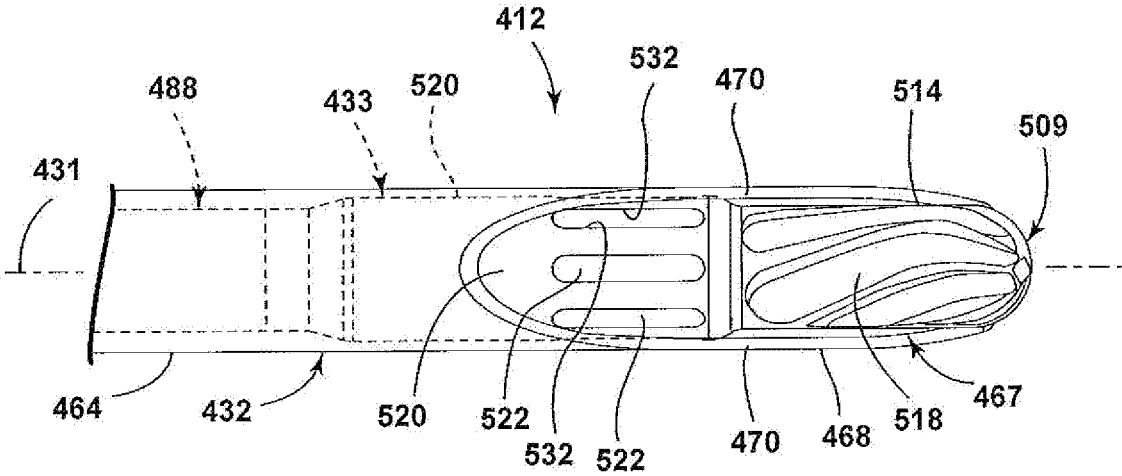
FIG. 15 is an enlarged and fragmentary view of the distal end of the surgical accessory of the third embodiment with the inner cutting element rotated approximately 180 degrees from the position shown in FIG. 14.

FIGS. 14 and 15 illustrate a third embodiment of the surgical accessory. Components of the third embodiment which are similar or identical to components of the first embodiment of the surgical accessory 12 will include the same reference numbers as in the prior embodiment, plus "400", and a detailed description of all components will therefore not be provided. The surgical accessory 412 according to the second embodiment includes an inner cutting element 433 rotatably disposed within an outer housing element 432. The inner cutting element 433 incorporates a drive shaft assembly including a drive shaft 488 having a distal end 491 with a cutting head 504. The tubular neck portion 507 of the cutting head 504 defines therein a plurality, and here eight, of suction openings 522 which open outwardly through the bearing surface 520 of the neck portion 507. These suction openings 522 are substantially identical to one another and each is configured as a longitudinally elongated slot which extends in a substantially linear manner longitudinally along the bearing surface 520 substantially parallel to the axis 431 of the accessory 412. In the illustrated embodiment, the suction openings 522 are uniformly circumferentially spaced from one another about the neck portion 507. Each of the suction openings 522 extends completely through the wall 511 for communication with the suction passage 512 of the cutting head 504 and the suction passage 489 of the drive shaft 488. Each of the suction openings 522 has a pair of opposed edges 532 disposed at the bearing surface 520.

The inner cutting element 433 is housed within the outer housing element 432 and the assembled accessory 412 is secured to the handpiece 11. As shown in FIG. 15, with the cutting element 433 disposed within the outer housing element 432, the cutting head 504 and the bearing surface 520 are positioned adjacent the window 467 of the housing element 432 so that at least a portion of the cutting head 504 and one or more of the suction openings 522 are exposed through the window 467. Further, with the cutting element 433 assembled to the housing element 432, the edges 470 of the housing tube 464 operate to wipe debris away from the suction openings 522. If the edges 532 of the suction openings 522 and/or the edges 470 of the housing tube 464 are configured as cutting edges, then the cutting edges 532 cooperate with the cutting edges 470 of the housing tube 464 to cut tissue should this be necessary.

FIGS. 16-18 illustrate a fourth embodiment of the surgical accessory. Components of the fourth embodiment which are similar or identical to components of the first embodiment of the surgical accessory 12 will include the same reference numbers as in the prior embodiment, plus "600", and a detailed description of all components will not be provided. The surgical accessory 612 according to the fourth embodiment includes an inner cutting element 633 rotatably disposed within an outer housing element 632. The inner cutting element 633 incorporates a drive shaft assembly including a drive shaft 688 having a distal end 691 with a cutting head 704. The tubular neck portion 707 of the cutting head 704 defines therein a plurality, and here ten, of suction openings 722 which open outwardly through the bearing surface 720 of the neck portion 707. These suction openings 722 are substantially identical to one another and each is configured as a slot which is elongated in a direction transverse to the axis 631. Each suction opening 722 has an arc length or a circumferential extent which is less than 180 degrees, and the suction openings 722 are provided in diametrically opposed pairs in an axial direction along the bearing surface 720 with the openings 722 of each opposed pair of openings being separated from one another by a pair of diametrically opposed bridge sections 729 of the wall 711 of the neck portion 607. In the illustrated embodiment, the bridge sections 729 of each pair of opposed suction openings 722 are circumferentially offset from the respective bridge sections 729 of the axially-adjacent pair or pairs of opposed suction openings 722 by approximately ninety degrees. Further, the opposed pairs of suction openings 722 are spaced axially from one another in a substantially uniform manner along the bearing surface 720. Each of the suction openings 722 extends completely through the wall 711 of the neck portion 707 for communication with the suction passage 712 of the cutting head 704 and the suction passage 689 of the drive shaft 688. Further, each of the suction openings 722 has a pair of opposed edges 732 disposed at the bearing surface 720.

The inner cutting element 633 is housed within the outer tubular housing element 632 and the assembled accessory 612 is secured to the handpiece 11. As shown in FIG. 18, with the cutting element 633 disposed within the outer housing element 632, the cutting head 704 and the bearing surface 720 are positioned adjacent the window 667 of the housing element 632 so that at least a portion of the cutting head 704 and one or more of the suction openings 722 are exposed through the window 667. Further, with the cutting element 633 assembled to the housing element 632, the edges 670 of the housing tube 664 wipe away debris from the suction openings 722 as in the prior embodiments. If the edges 732 of the suction openings 722 and/or the edges 670 of the housing tube 664 have cutting geometries, the cutting edges 732 of the suction openings 722 cooperate with the cutting edges 670 of the housing tube 664 to cut tissue adjacent the cutting head 704.

Figure 19:
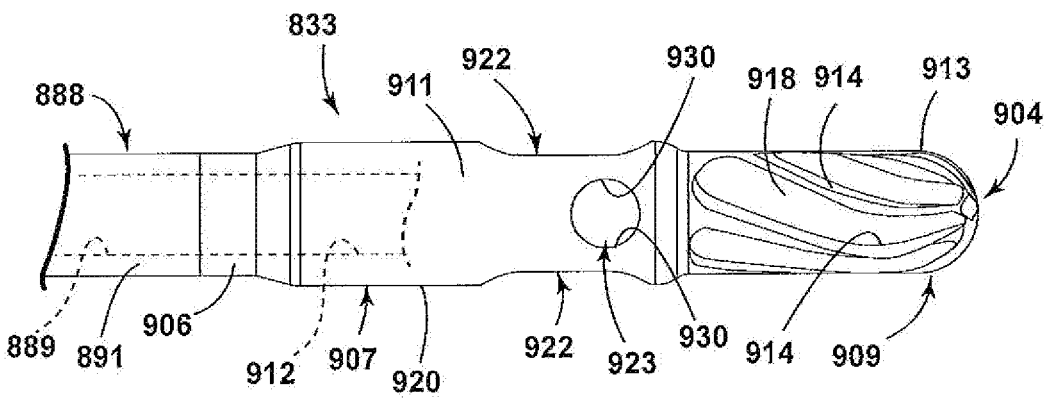
FIG. 19 is an enlarged and fragmentary top view of the distal end of the inner cutting element of a fifth embodiment of the surgical accessory.
Figure 20:
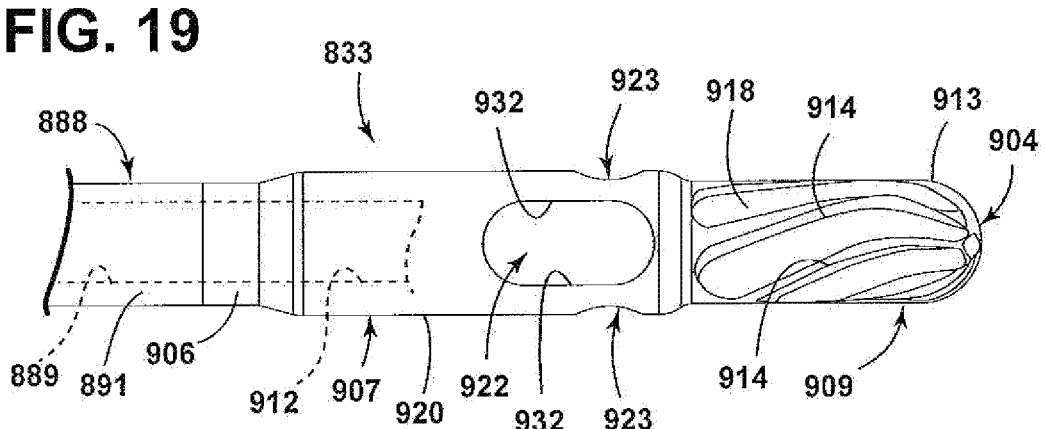
FIG. 20 is an enlarged and fragmentary view of the distal end of the inner cutting element of the fifth embodiment of the surgical accessory, with the inner cutting element rotated approximately 90 degrees from the position shown in FIG. 19.
Figure 21:
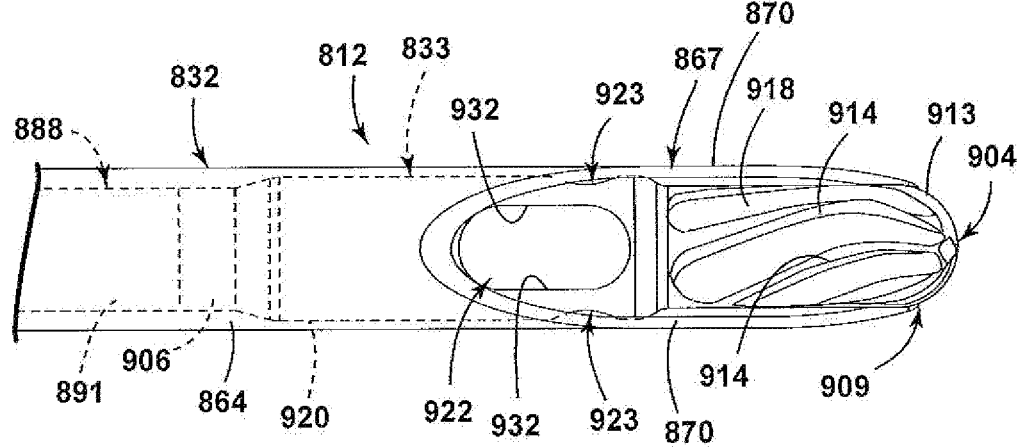
FIG. 21 is an enlarged and fragmentary view of the distal end of the surgical accessory of the fifth embodiment.

FIGS. 19-21 illustrate a fifth embodiment of the surgical accessory. Components of the fifth embodiment which are similar or identical to components of the first embodiment of the surgical accessory 12 will include the same reference numbers as in the prior embodiment, plus "800", and a detailed description of all components will accordingly not be provided. The surgical accessory 812 according to the fifth embodiment includes an inner cutting element 833 rotatably disposed within an outer housing element 832. The inner cutting element 833 incorporates a drive shaft assembly including a drive shaft 888 having a distal end 891 with a cutting head 904. The tubular neck portion 907 of the cutting head 904 defines therein a plurality, and here four, of suction openings 922 and 923 disposed within the wall 911 which open outwardly through the bearing surface 920 of the neck portion 907. The suction openings 922 and 923 are oriented in circumferentially spaced relation with one another about the neck portion 907, and in the illustrated embodiment the suction openings 922 and 923 are spaced at approximately 90 degree intervals from one another along the circumference of the neck portion 907. Two of the suction openings 922 are configured as longitudinally elongated holes and these suction openings 922 are diametrically opposed to one another (approximately 180 degrees from one another) and are axially aligned with one another, and the remaining two suction openings 923 are axially aligned with one another and are diametrically opposed one another on the neck portion 907. The suction openings 923 in the illustrated embodiment are configured as circular holes. Each of the suction openings 922 and 923 extends completely through the wall 911 for communication with the suction passage 912 of the cutting head 904 and the suction passage 889 of the drive shaft 888. Each suction opening 922 has a pair of opposed edges 932 disposed at the bearing surface 920, and each suction opening 923 has a pair of opposed edges 930 disposed at the bearing surface 920. In the illustrated embodiment, the suction openings 922, due to their longitudinally elongated shape, extend over a greater axial distance than the suction openings 923.

The inner cutting element 833 is housed within the outer tubular housing element 832 and the assembled accessory 812 is secured to the handpiece 11. As shown in FIG. 21, with the cutting element 833 disposed within the outer housing element 832, the cutting head 904 and the bearing surface 920 are positioned adjacent the window 867 of the housing element 832 so that at least a portion of the cutting head 904 and one or more of the suction openings 922 and 923 are exposed through the window 867. Further, with the cutting element 833 assembled to the housing element 832, the edges 870 act to wipe away debris from the suction openings 922 and 932. If the edges 932 and 930 and/or the edges 870 of the housing tube 864 are configured as cutting edges, then the cutting edges 932 and 930 of the suction openings 922 and 923 cooperate with the cutting edges 870 of the housing tube 864 to cut tissue should this be necessary due to a buildup of surgical debris adjacent the cutting head 904.

Figure 22:
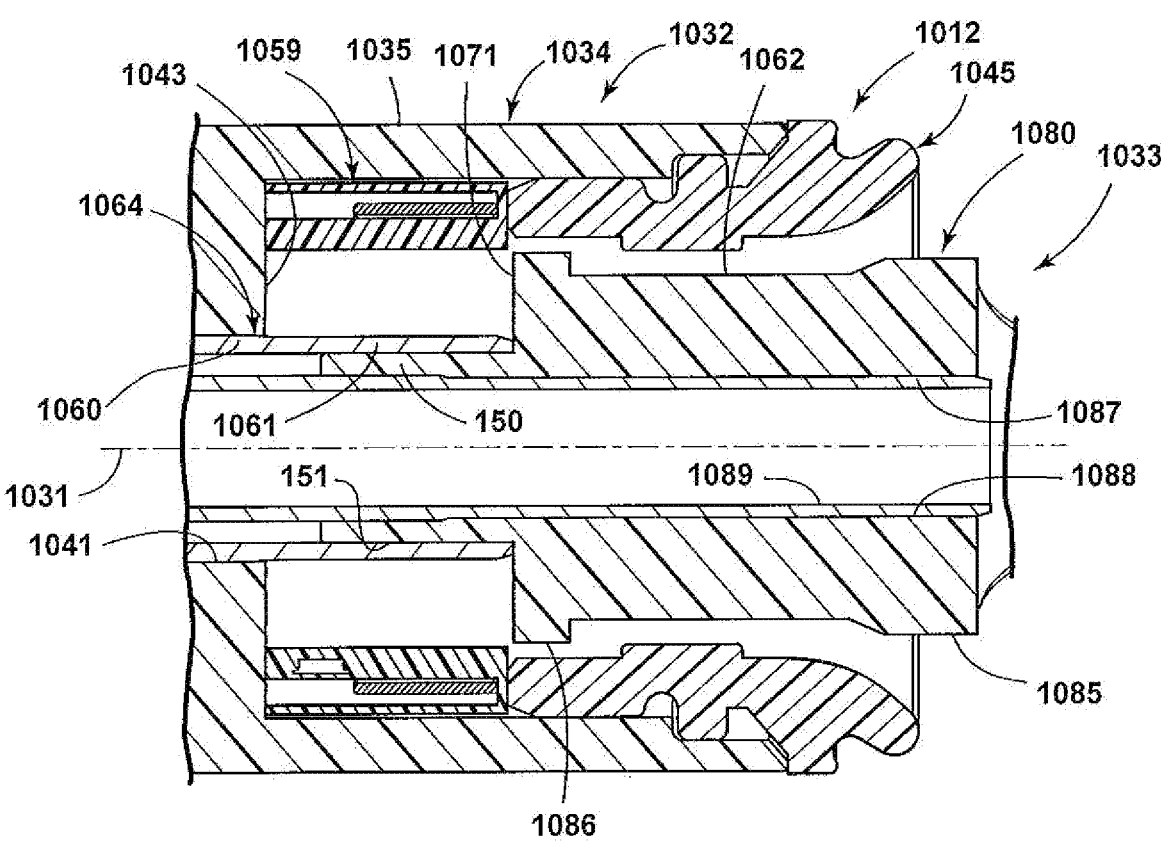
FIG. 22 is an enlarged and fragmentary longitudinal cross-section of a sixth embodiment of the surgical accessory.
Figure 23:
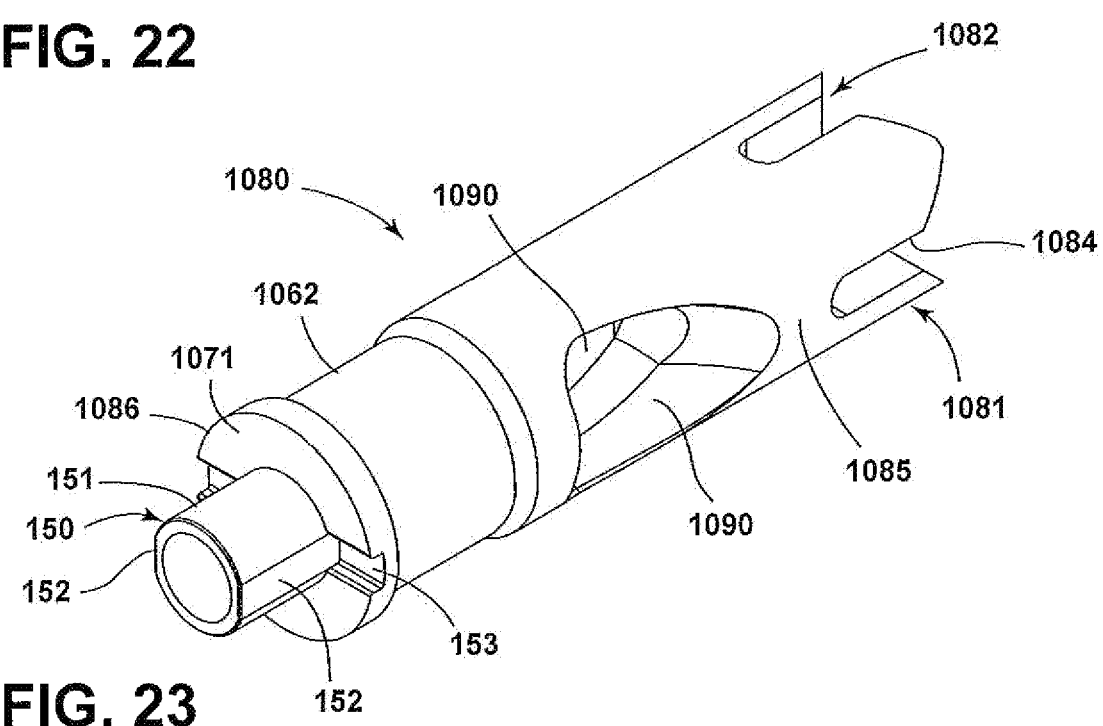
FIG. 23 is an enlarged perspective view of the hub, in isolation, of the inner cutting element of the sixth embodiment.

FIGS. 22 and 23 illustrate a sixth embodiment of the surgical accessory. Components of the sixth embodiment which are similar or identical to components of the first embodiment will include the same reference numbers as in the first embodiment, plus "1000", and a detailed description of all components will accordingly not be provided. The surgical accessory 1012 according to the sixth embodiment incorporates an alternative configuration of the hub of the inner cutting element which accommodates a larger diameter housing tube of the outer housing element. In this regard, the hub 1080 of the inner cutting element 1033 of this embodiment includes a substantially cylindrical protrusion 150 which extends axially in the distal direction from the neck 1086 of the hub 1080 and has a smaller outer diameter than the outer diameter of the neck 1086. The neck 1086 and the protrusion 150 are joined to one another by a shoulder 1071 which faces in the distal direction and extends transversely relative to the axis 1031 between the protrusion 150 and the neck 1086. The hub bore 1087 in this embodiment has a substantially constant inner diameter and opens proximally through the drive element 1081 and distally through the protrusion 150. As best shown in FIG. 23, the protrusion 150 has an outer surface 151 which defines therein a pair longitudinally extending chamfers or flats 152 which extend from the distal terminal end of the protrusion 150 to the head 1086. Further, the head 1086 defines therein a pair of transversely extending channels 153 which extend radially outwardly from respective inner ends of the flats 152 and open radially through the head 1086.

The housing tube 1064 of the outer housing element 1032 in this embodiment, as in the first embodiment, has a proximal end 1060 which is induction bonded to the hub 1034, which hub 1034 has a large induction core through which the proximal end 1060 extends via the bore 1041. The proximal end 1060 extends in the proximal direction axially beyond the shoulder 1043 of the hub 1034 so as to have an exposed free end 1061 which extends over the outer surface 151 of the protrusion 150 of the hub 1080 of the inner cutting element 1033.

When the cutting element 1033 is fully inserted into housing element 1032, the free end 1061 of the housing tube 1064 extends over the protrusion 150 like a sleeve, and the free terminal end 1061 of the housing tube 1064 abuts axially against the shoulder 1071, as shown in FIG. 22. The outer diameter of the outer surface 151 of the protrusion 150 is slightly smaller than the inner diameter of the free end 1061 so as to allow the insertion of the protrusion 150 thereinto and such that there is only a small radial clearance between the inner surface of the free end 1061 and the outer surface 151. The radial engagement of the outer surface 151 with the inner surface of the free end 1061 of the housing tube 1064 and the axial engagement of the free terminal end 1061 of the housing tube 1064 with the shoulder 1071 provides both a radial bearing and an axial bearing, respectively, at the proximal end of the surgical accessory 1012. When the accessory 1012 is mounted to the handpiece 11, a spring (not shown here, but similar to the spring 75) provided within the drive element 1081 of the cutting element 1033 cooperates with the handpiece 11 and biases the cutting element 1033 in the distal direction relative to the outer housing element 1032, which serves to maintain the free or terminal end 1061 of the housing tube 1064 against the shoulder 1071. The mating areas between the inner surface of the free end 1061 of the housing tube 1064 and the outer surface 151 of the protrusion 150 can be provided with lubricant in order to minimize friction between these components during movement of the inner cutting element 1033 relative to the outer housing element 1032. In this regard, lubricant can be applied to the flats 152 and/or the channels 153 so as to lubricate the areas between the housing tube 1064 and the hub 1080.

Although particular preferred embodiments of the invention are disclosed in detail for illustrative purposes, it will be recognized that variations or modifications of the disclosed apparatus, including the rearrangement of parts, lie within the scope of the present invention.

The invention claimed is:
1. A surgical cutting accessory comprising:
an outer shaft extending along a longitudinal axis from a
   proximal end of the outer shaft to a distal end of the
   outer shaft, the outer shaft having a window at the distal
   end of the outer shaft; and an inner cutting shaft extending along the longitudinal axis from a proximal end of the inner cutting shaft to a distal end of the inner cutting shaft, the inner cutting shaft being disposed within the outer shaft such that the inner cutting shaft is rotatable within the outer shaft, the inner cutting shaft comprising:

a bearing portion having an outer bearing surface in operative communication with an inner surface of the outer shaft;

a suction opening extending through a wall of the inner cutting shaft into the inner cutting shaft; and a cutting head extending along the longitudinal axis to the distal end of the inner cutting shaft such that the bearing portion is in between the proximal end of the inner cutting shaft and the cutting head, wherein the suction opening is proximate to the cutting head and is exposed through the window of the outer shaft in at least some rotational positions of the inner cutting shaft, and wherein the window of the outer shaft extends along the longitudinal axis such that at least part of the window and at least part of the cutting head are a first distance from the proximal end of the inner cutting shaft, wherein the suction opening is positioned such that a distal part of the bearing portion is in between the suction opening and the cutting head.

2. The surgical cutting accessory of claim 1, wherein at least one of the inner surface of the outer shaft and the outer bearing surface of the bearing portion are wear-resistant.

3. The surgical cutting accessory of claim 2, wherein the wear resistance of the at least one of the inner surface of the outer shaft and the outer bearing surface of the bearing portion is provided through a coating of a wear-resistant material.

4. The surgical cutting accessory of claim 1, wherein the bearing portion is in between a proximal inner shaft portion and the cutting head, and a first diameter of the bearing portion is greater than a second diameter of the proximal inner shaft portion.

5. The surgical cutting accessory of claim 1, wherein the bearing portion and the cutting head are part of a single monolithic component of the inner cutting shaft.

6. The surgical cutting accessory of claim 1, wherein the inner surface of the outer shaft and the outer bearing surface of the bearing portion are stainless steel.

7. The surgical cutting accessory of claim 1, wherein the bearing portion and the cutting head are disposed in a distal portion of the outer shaft and the inner surface of the outer shaft is defined by a first radius throughout the distal portion of the outer shaft, a majority of the cutting head and a sub-portion of the distal portion of the outer shaft extending together over a single distance along the longitudinal axis.

8. The surgical cutting accessory of claim 1, wherein the suction opening is defined in part by an outer edge abutting the bearing portion.

9. The surgical cutting accessory of claim 8, wherein the bearing portion at the outer edge has a first diameter that is a maximum diameter of the inner cutting shaft.

10. A surgical cutting accessory comprising:

an outer shaft extending along a longitudinal axis from a proximal end of the outer shaft to a distal end of the outer shaft, the outer shaft having a window at the distal end of the outer shaft; and an inner cutting shaft extending along the longitudinal axis from a proximal end of the inner cutting shaft to a distal end of the inner cutting shaft, the inner cutting shaft being disposed within the outer shaft such that the inner cutting shaft is rotatable within the outer shaft, the inner cutting shaft comprising:

an intermediate portion spaced apart from the proximal end of the inner cutting shaft, the intermediate portion having an outer bearing surface cooperating with an inner surface of the outer shaft, a sub-portion of the outer bearing surface being exposed through the window in at least some rotational positions of the inner cutting shaft;

a suction opening; and a cutting head extending along the longitudinal axis to the distal end of the inner cutting shaft such that the intermediate portion is in between the proximal end of the inner cutting shaft and the cutting head, the cutting head being exposed through the window such that part of the cutting head faces the outer shaft, wherein the suction opening is exposed through the window of the outer shaft in at least some rotational positions of the inner cutting shaft.

11. The surgical cutting accessory of claim 10, wherein at least one of the inner surface of the outer shaft and the outer bearing surface of the intermediate portion are wear-resistant.

12. The surgical cutting accessory of claim 11, wherein the wear resistance of the at least one of the inner surface of the outer shaft and the outer bearing surface of the intermediate portion is provided through a coating of a wear-resistant material.

13. The surgical cutting accessory of claim 10, wherein the intermediate portion is in between a proximal portion of the inner cutting shaft and the cutting head, and a first diameter of the intermediate portion is greater than a second diameter of the proximal portion.

14. The surgical cutting accessory of claim 10, wherein the intermediate portion and the cutting head are part of a single monolithic component of the inner cutting shaft.

15. The surgical cutting accessory of claim 10, wherein the inner surface of the outer shaft and the outer bearing surface of the intermediate portion are stainless steel.

16. The surgical cutting accessory of claim 10, wherein the intermediate portion and the cutting head are disposed in a distal portion of the outer shaft, and the inner surface of the outer shaft has a first diameter throughout the distal portion of the outer shaft.

17. The surgical cutting accessory of claim 10, wherein the intermediate portion has a first diameter that is a maximum diameter of the inner cutting shaft.

18. A method of operating a surgical cutting accessory comprising:

providing a surgical cutting accessory comprising:

an outer shaft extending along a longitudinal axis from a proximal end of the outer shaft to a distal end of the outer shaft, the outer shaft having a window at the distal end of the outer shaft; and an inner cutting shaft extending along the longitudinal axis from a proximal end of the inner cutting shaft to a distal end of the inner cutting shaft, the inner cutting shaft being disposed within the outer shaft such that the inner cutting shaft is rotatable within the outer shaft, the inner cutting shaft comprising:

a bearing portion having an outer bearing surface in operative communication with an inner surface of the outer shaft;

a suction opening extending through a wall of the inner cutting shaft into the inner cutting shaft; and a cutting head extending along the longitudinal axis to the distal end of the inner cutting shaft such that the bearing portion is in between the proximal end
of the inner cutting shaft and the cutting head, wherein the suction opening is proximate to the cutting
head and is exposed through the window of the outer
shaft in at least some rotational positions of the inner
cutting shaft, wherein the window of the outer shaft extends along
the longitudinal axis such that at least part of the
window and at least part of the cutting head are a first
distance from the proximal end of the inner cutting
shaft, and wherein the suction opening is positioned such that a
distal part of the bearing portion is in between the
suction opening and the cutting head, bringing the surgical cutting accessory into contact with
tissue at a surgical site of a patient; and actuating the inner cutting shaft such that the inner cutting
shaft rotates about the longitudinal axis and displaces at
least some tissue at the surgical site.

19. The method of claim 18, further comprising position-
ing the cutting head to remove target tissue at the surgical
site such that any removed tissue collected proximate the
suction opening is cut by interaction between an edge of the
window and an edge of the suction opening to prevent
blockage of the suction opening.

\* \* \* \* \*